US010695734B2

(12) United States Patent
Fuchs et al.

(10) Patent No.: US 10,695,734 B2
(45) Date of Patent: Jun. 30, 2020

(54) MICROCAPSULE COMPRISING A POLYESTER-URETHANE SHELL AND A HYDROPHILIC CORE MATERIAL

(71) Applicant: BASF SE, Ludwigshafen am Rhein (DE)

(72) Inventors: Yannick Fuchs, Speyer (DE); Helmut Witteler, Wachenheim (DE); Matthias Bratz, Maxdorf (DE)

(73) Assignee: BASF SE, Ludwigshafen am Rhein (DE)

( * ) Notice: Subject to any disclaimer, the term of this patent is extended or adjusted under 35 U.S.C. 154(b) by 22 days.

(21) Appl. No.: 15/777,334

(22) PCT Filed: Nov. 8, 2016

(86) PCT No.: PCT/EP2016/076945
§ 371 (c)(1),
(2) Date: May 18, 2018

(87) PCT Pub. No.: WO2017/089115
PCT Pub. Date: Jun. 1, 2017

(65) Prior Publication Data
US 2018/0353924 A1 Dec. 13, 2018

(30) Foreign Application Priority Data
Nov. 23, 2015 (EP) ..................... 15195834

(51) Int. Cl.
| | | |
|---|---|---|
| *A61K 8/11* | (2006.01) | |
| *A01N 25/28* | (2006.01) | |
| *B01J 13/16* | (2006.01) | |
| *A61Q 19/00* | (2006.01) | |
| *A61K 8/87* | (2006.01) | |
| *A61K 9/50* | (2006.01) | |
| *B01J 13/14* | (2006.01) | |

(52) U.S. Cl.
CPC .............. *B01J 13/16* (2013.01); *A01N 25/28* (2013.01); *A61K 8/11* (2013.01); *A61K 8/87* (2013.01); *A61K 9/5031* (2013.01); *A61K 9/5089* (2013.01); *A61Q 19/00* (2013.01); *B01J 13/14* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 3,779,932 A | 12/1973 | Wagner et al. | |
| 3,849,326 A | 11/1974 | Wagner et al. | |
| 4,042,768 A | 8/1977 | Muller et al. | |
| 4,145,184 A | 3/1979 | Brain et al. | |
| 4,152,272 A | 5/1979 | Young | |
| 4,209,417 A | 6/1980 | Whyte | |
| 4,379,071 A | 4/1983 | Schnoering Hildegard et al. | |
| 4,515,705 A | 5/1985 | Moeddel | |
| 4,524,018 A | 6/1985 | Yemoto et al. | |
| 4,879,361 A | 11/1989 | Rehmer et al. | |
| 4,994,266 A | 2/1991 | Wells et al. | |
| 5,081,000 A | 1/1992 | Kuehn et al. | |
| 5,108,654 A | 4/1992 | Ragaini | |
| 5,378,468 A | 1/1995 | Suffis et al. | |
| 5,969,030 A | 10/1999 | Grandhee et al. | |
| 2003/0157170 A1 | 8/2003 | Liggins et al. | |
| 2017/0042143 A1 | 2/2017 | Burakowska-Meise et al. | |
| 2017/0114154 A1 | 4/2017 | Shabelina et al. | |
| 2017/0318811 A1 | 11/2017 | Mecfel-Marczewski et al. | |
| 2017/0360660 A1 | 12/2017 | Burakowska-Meise et al. | |

FOREIGN PATENT DOCUMENTS

| | | |
|---|---|---|
| CN | 101109151 A | 1/2008 |
| DE | 1081228 B | 5/1960 |
| DE | 3026831 A1 | 2/1982 |
| DE | 3046476 A1 | 7/1982 |
| DE | 3709921 A1 | 10/1988 |
| EP | 0780154 A1 | 6/1997 |
| EP | 2426172 A1 | 3/2012 |
| EP | 2648211 A1 | 10/2013 |
| GB | 2250930 A | 6/1992 |
| JP | H05230496 A | 9/1993 |
| JP | H07179328 A | 7/1995 |
| WO | 8202387 A1 | 7/1982 |
| WO | 9504809 A1 | 2/1995 |
| WO | 9516660 A1 | 6/1995 |
| WO | 9614827 A1 | 5/1996 |
| WO | 9638528 A1 | 12/1996 |
| WO | 03015910 A1 | 2/2003 |
| WO | 03061817 A1 | 7/2003 |
| WO | 2006044305 A1 | 4/2006 |

(Continued)

OTHER PUBLICATIONS

Roy et al., Controlled pesticide release from biodegradable polymers, Cent. Eur. J. Chem. • 12(4) • 2014 • 453-469 (Year: 2014).*
Sun et al., Encapsulation and controlled release of hydrophilic pesticide in shell cross-linked nanocapsules containing aqueous core, International Journal of Pharmaceutics 463 (2014) 108-114 (Year: 2014).*
Huiru, Zhang et al., Machine Translation of CN 101109151, Jan. 23, 2008 (Year: 2008).*

(Continued)

*Primary Examiner* — Jennifer A Berrios
(74) *Attorney, Agent, or Firm* — Armstrong Teasdale LLP

(57) ABSTRACT

Provided herein are microcapsules as core-shell-particles, including a polymeric shell, a method of making them, a dispersion of the microcapsules in a liquid medium and a method of using thereof. The microcapsules include a core that contains a hydrophilic component.

20 Claims, No Drawings

(56) References Cited

FOREIGN PATENT DOCUMENTS

| WO | 2006048166 A1 | 5/2006 |
|---|---|---|
| WO | 2006048169 A1 | 5/2006 |
| WO | 2008033224 A1 | 3/2008 |
| WO | 2010134044 A2 | 11/2010 |
| WO | 2011160733 A1 | 12/2011 |
| WO | 2011161229 A1 | 12/2011 |
| WO | 2013182855 A2 | 12/2013 |
| WO | WO-2015/091642 A1 | 6/2015 |
| WO | 2015132707 A1 | 9/2015 |
| WO | WO-2015/165834 A1 | 11/2015 |
| WO | WO-2017/021159 A1 | 2/2017 |
| WO | WO-2017/029302 A1 | 2/2017 |
| WO | WO-2017/037210 A1 | 3/2017 |
| WO | WO-2017/068024 A1 | 4/2017 |

OTHER PUBLICATIONS

Database WPI, Week 200872, Thomson Scientific, London, GB, AN 2008-M13444, XP002757852.

European Search Report for EP Patent Application No. 15195834.5, dated Aug. 30, 2016, 4 pages.

International Search Report for PCT Patent Application No. PCT/EP2016/076946, dated Dec. 7, 2016, 4 pages.

International Search Report and Written Opinion for International Application No. PCT/EP2016/076945, dated Dec. 14, 2016, 10 pages.

\* cited by examiner

MICROCAPSULE COMPRISING A POLYESTER-URETHANE SHELL AND A HYDROPHILIC CORE MATERIAL

CROSS-REFERENCE TO RELATED APPLICATIONS

This application is the national stage entry of PCT/EP2016/076945, filed on Nov. 8, 2016, which claims the benefit of priority to European Patent Application No. 15195834.5, filed Nov. 23, 2015, which are incorporated by reference in their entirety herein.

FIELD OF THE INVENTION

The present invention relates to microcapsules as a core-shell-particles, comprising a polymeric shell, a method of making them, a dispersion of those microcapsules in a liquid medium and the use thereof. The microcapsules comprise a core that contains a hydrophilic component.

BACKGROUND

Microcapsules are spherical objects which consist of a core and a wall material surrounding the core, wherein the core in principal can be a solid, liquid or gaseous component which is surrounded by the solid wall material. For many applications the wall is formed by a polymer material. Microcapsules usually have a volume average diameter from 1 to 1000 µm.

A multitude of shell materials is known for producing the wall of microcapsules. The shell can consist either of natural, semisynthetic or synthetic materials. Natural shell materials are, for example, gum arabic, agar agar, agarose, maltodextrins, alginic acid or its salts, e.g. sodium alginate or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic shell materials are inter alia chemically modified celluloses, in particular cellulose esters and cellulose ethers, e.g. cellulose acetate, ethyl cellulose, hydroxypropylcellulose, hydroxypropylmethylcellulose and carboxymethyl-cellulose, and also starch derivatives, in particular starch ethers and starch esters. Synthetic shell materials are, for example, polymers, such as polyacrylates, polyamides, polyvinyl alcohols, polyvinylpyrrolidones or polyureas.

Depending on the type of shell material and the production process, microcapsules are formed in each case with different properties, such as diameter, size distribution and physical and/or chemical properties.

Polyurea core-shell microcapsules obtained by reaction of at least one diisocyanate and at least one polyamine are well known in the art, for example from WO 2011/161229 or WO 2011/160733. According to WO 2011/161229 or WO 2011/160733 the polyurea microcapsules are prepared in presence of polyvinylpyrrolidone (PVP) as a protective colloid.

The development of biodegradable microcapsules was carried out mainly for drug transport and in-vivo release applications. Attention toward biodegradable capsules was increased since environmental aspects of polymers started to be discussed in the public and efforts were made to reduce environmental pollution.

Generally polyurethanes are prepared by reacting a polyisocyanate with a polyol component. Typical polyols employed in the preparation of polyurethanes are polyether polyols or polyester polyols. There is still a demand for polyurethanes that are suitable as polymeric shell material in microcapsules. For certain applications it would be advantageous that said shell material apart from having good application properties is also biodegradable.

WO 2006/044305 relates to an isocyanate-terminated prepolymer composition obtained by reaction of methylene diphenylisocyanate with a polycaprolactone polyol. The obtained prepolymer is used in the manufacture of polyurethane or polyurea elastomers.

WO 2008/033224 relates to isocyanate-terminated polycaprolactone polyurethane prepolymers obtained by reaction of toluene diisocyanate and a polyol composition. The obtained prepolymer can reacted with an amine chain extender resulting in polyurethane elastomers.

WO 03/061817 relates to substrates coated with polymers, containing microcapsules in the polymer layer, wherein the polymers includes for example polyurethanes, polyurethaneureas, polyacrylonitriles or copolymers of styrene.

U.S. Pat. No. 4,379,071 relates to a process for the production of microcapsules, wherein a diol or polyol which has a molecular weight of 400 to 10000 g/mol reacts with phosgene or a diisocyanate which contains at least two chloroformic acid esters or isocyanate groups per molecule. The resulting reaction product of those components is mixed with the desired core material and a chain lengthening agent which is at least bifunctional.

EP 0780154 relates to a process for preparing biodegradable microcapsules wherein the microcapsules are made by the addition reaction between polyamines, in particular aliphatic primary or secondary di- or polyamines, and polyisocyanate components containing at least one bifunctional isocyanate with an average of at least one ester and/or amide group in the main chain.

However, there continues to be a need for microcapsules, wherein the size of the micropasules can be controlled in a wide range and that are capable of releasing an encapsulated ingredient under controlled conditions. There is also a demand for microcapsules which have at least one encapsulated hydrophilic component, wherein the microcapsules have enhanced stability against leaking of the encapsulated components from the capsules. Delayed release of the encapsulated active ingredients for crop protection, personal care compositions or pharmaceutical compositions, is also of interest.

DESCRIPTION

It is an object of the present invention to provide a microcapsule, wherein the shell comprises a polymer containing polyurethane and/or polyurea groups, which can be prepared by reactive microencapsulation, in particular by in situ radical polymerization, polyaddition or polycondensation. It is a further object of the present invention to provide such microcapsules wherein the shell of the microcapsules has the afore-mentioned desired properties and containing a hydrophilic component as core material. In a further variant the microcapsules should be provided as an "inverse" dispersion, comprising microcapsules containing at least one hydrophilic core material in an hydrophobic (lipophilic) medium as the continuous phase.

Further, it is an object of the present invention to provide microcapsules for the use as or in a personal care composition, as or in a composition used for industrial or institutional or hospital disinfection, as or in a material protection composition, as or in a pharmaceutical composition, as or in a plant protection composition, as or in home care products.

Last but not least, it is an object of the present invention to provide a microcapsule compositions having biodegradable segments embedded in the capsule wall.

Surprisingly, these objects could be achieved by microcapsules, wherein the core comprises at least one hydrophilic or at least one hydrophobic component and wherein the shell of the microcapsules comprises polyurea and/or polyurethane linkages. In particular, the shell material of the microcapsules according to the invention comprises a poly (ester-urethane) in polymerized form.

The present invention relates to microcapsule comprising a capsule core and a polymeric shell, wherein the core essentially contains only hydrophilic components and the shell comprises in polymerized form A) at least one poly(ester-urethane) containing at least 2 isocyanate groups, obtainable by reacting at least one polyester-polyol containing at least 2 OH groups with at least one polyisocyanate containing at least 2 NCO groups, and
B) at least one compound which comprises at least 2 terminal groups which are reactive towards isocyanate-groups, which are selected from OH, NHR, or SH, wherein R is selected from hydrogen, alkyl, cycloalkyl or aryl.

The present invention further relates to a microcapsule dispersion, comprising microcapsules wherein the capsule core contains essentially hydrophilic components, obtainable by a) providing a premix (Ia) comprising the hydrophilic component(s) to be encapsulated (Ca), optionally a hydrophilic medium that is liquid at 20° C. and 1023 mbar different from (Ca), and at least one component (B) which is defined above and below, and
b) mixing the premix (Ia) provided in step a) with an hydrophobic medium (IIa) comprising at least one hydrophobic protective colloid, at least one component (A), which is defined above and below, and reacting the resulting mixture to form microcapsules dispersed in the hydrophobic medium (IIa).

The present invention further relates to a process for the preparation of the microcapsule dispersion, comprising microcapsules according to the invention, wherein the capsule core contains essentially hydrophilic components, comprising the steps:

a) providing a premix (Ia) comprising the hydrophilic component(s) to be encapsulated (Ca), optionally a hydrophilic medium that is liquid at 20° C. and 1023 mbar different from (Ca), and at least one component (B) as defined above and below,
b) mixing the premix (Ia) provided in step a) with an hydrophobic medium (IIa) comprising at least one hydrophobic protective, at least one component (A) as defined above and below, and reacting the resulting mixture to form microcapsules dispersed in the hydrophobic medium (IIa).

The present invention further relates to a microcapsule obtained by the processes according to the invention. The present invention further relates to microcapsules obtained by the processes according to the invention in dry form. The present invention further relates to the use of microcapsules or microcapsules according to the invention or obtained by the processes according to the invention in a personal care composition, or a home care composition, or a composition used for industrial or institutional or hospital applications, or a material protection composition, or a pharmaceutical composition, or a plant protection composition. The present invention further relates to the use of the microcapsules according to the invention or obtained by the processes according to the invention in a cosmetic composition, a hygiene composition, a composition for industrial or institutional or hospital cleaning or disinfection, laundry detergents, fabric softeners, dishwashing liquids, household cleaners, industrial cleaners, oil recovery, adhesives, coatings, or constructions, or agro formulations.

The microcapsules according to the invention have the following advantages:
Small particle size and narrow particle size distribution
Good tightness and mechanical stability
Sprayable
Partially made out of biodegradable building blocks The terms "biodegradation" or "biodegradability" are synonyms and mean in the sense of the invention that the polymers decompose in an appropriate and demonstrable period of time when exposed to the effects of the environment. The degradation mechanism can be hydrolytic and/or oxidative, and is based mainly on exposure to microorganisms, such as bacteria, yeasts, fungi, and algae. An example of a method for determining biodegradability mixes the polymer with compost and stores it for a particular time. According to ASTM D5338, ASTM D6400, EN 13432, and DIN V 54900, $CO_2$-free air, by way of example, is passed through ripened compost during the composting process, and this compost is subjected to a defined temperature program. Biodegradability is defined here by way of the ratio of the net to amount of $CO_2$ liberated from the specimen (after deducting the amount of $CO_2$ liberated by the compost without the specimen) to the maximum possible amount of $CO_2$ liberated by the specimen (calculated from the carbon content of the specimen). Even after a few days of composting, biodegradable polymers generally show marked signs of degradation, for example fungal growth, cracking, and perforation.

In another method of determining biodegradability, the polymer is incubated with a certain amount of a suitable enzyme at a certain temperature for a defined period, and then the concentration of the organic degradation products dissolved in the incubation medium is determined. By way of example, by analogy with Y. Tokiwa et al., American Chemical Society Symposium 1990, Chapter 12, "Biodegradation of Synthetic Polymers Containing Ester Bonds", the polymer can be incubated for a number of hours at from 30 to 37° C. with a predetermined amount of a lipase, for example from *Rhizopus arrhizus, Rhizopus delemar, Achromobacter* sp., or *Candida cylindracea*, and the DOC value (dissolved organic carbon) can then be measured on the reaction mixture freed from insoluble constituents. For the purposes of the present invention, biodegradable polymers are those which after enzymatic treatment with a lipase from *Rhizopus arrhizus* for 16 h at 35° C. give a DOC value which is at least 10 times higher than that for the same polymer which has not been treated with the enzyme.

The term "functionality" represents, here and subsequently, the average number of the respective functional groups per molecule or per polymer chain.

The term "dispersion" is a system of at least two phases, wherein one of these phases is the continuous phase and at least one phase is dispersed. Dispersion is a generic term, which encompasses e.g. emulsions, wherein the continuous phase is liquid and the dispersed phase is liquid, suspensions wherein the continuous phase is liquid and the dispersed phase is solid, solid aerosole, wherein continuous phase is gas and the dispersed phase is solid.

In the context of the present invention, the expression "alkyl" comprises straight-chain and branched alkyl groups.

Suitable short-chain alkyl groups are, e.g. straight-chain or branched $C_1$-$C_7$ alkyl, preferably $C_1$-$C_6$ alkyl and particularly preferable $C_1$-$C_4$ alkyl groups. These include in particular methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, and the like. Suitable long-chain $C_8$-$C_{30}$ alkyl or $C_8$-$C_{30}$ alkenyl groups are straight-chain and branched alkyl or alkenyl groups. In this connection, they are preferably mainly linear alkyl residues, such as those also present in natural or synthetic fatty acids and fatty alcohols and also oxo alcohols, which, if appropriate, in addition can be mono-, di- or polyunsaturated. These include, e.g., n-hexyl(ene), n-heptyl(ene), n-octyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene), and the like.

Cycloalkyl preferably represents $C_5$-$C_8$ cycloalkyl, such as cyclopentyl, cyclohexyl, cycloheptyl or cyclooctyl. Aryl comprises unsubstituted and substituted aryl groups and preferably represents phenyl, tolyl, xylyl, mesityl, naphthyl, fluorenyl, anthracenyl, phenanthrenyl, naphthacenyl and in particular phenyl, tolyl, xylyl or mesityl.

The volume average particle size can be measured by light scattering measurements using a Malvern 2000S instrument and the Mie scattering theory.

Microcapsule

A first aspect of the invention relates to microcapsules per se.

One important parameter of the microcapsules of the invention is the shell weight of the capsules in relation to the total weight of the capsules. It is expressed as percentage of the shell weight with reference to the total weight of the capsules (=encapsulated lipophilic component+shell material).

The percentage of the shell weight with reference to the total weight of the capsules is of 5% to 40%, particularly 5% to 25%, and more particularly 10% to 20%.

The microcapsules of the microcapsule composition typically have core/shell ratios (w/w) from 20:1 to 1:10, preferably from 10:1 to 5:1 and in particular from 4:1 to 3:1.

A microcapsules of the microcapsule composition typically have the mean particle size d (0.5) from 0.5 µm to 50 µm, preferably from 0.7 µm to 30 µm, and in particular from 1 µm to 10 µm.

In a preferred form the microcapsules of the microcapsule composition typically have the mean particle size d (0.5) from 0.1 µm to 50 µm, preferably from 0.1 µm to 30 µm, and in particular from 0.2 µm to 10 µm.

In another preferred form the microcapsules of the microcapsule composition typically have the mean particle size d (0.5) from 0.1 µm to 1.0 µm, preferably from 0.1 µm to 0.8 µm, and in particular from 0.2 µm to 0.7 µm.

Within the context of the present invention, the microcapsules have a shell that is prepared by reacting at least one poly(ester-urethane) containing isocyanate groups (A) with at least one compound (B) (=variant 1), wherein compounds (B) comprise terminal groups which are reactive toward isocyanate-groups, and optionally further components capable of being incorporated into the shell. The reaction is a polyaddition between the isocyanate groups and a compound having at least one terminal group which is reactive toward isocyanate group, and optional further groups, capable of reacting with NCO groups, which leads to the formation of polyurethane and/or polyurea linkages. The compounds B) may, in addition to at least one primary or secondary amino group, contain at least one further group, capable of reacting with NCO groups, e.g. at least one OH group. Further components, capable of being incorporated into the shell are in principle all compounds which contain at least one active hydrogen atom per molecule. Reaction of NCO groups with amine groups leads to the formation of urea groups. Reaction of NCO groups with OH groups leads to the formation of urethane groups. Compounds containing only one active hydrogen atom per molecule lead to a termination of the polymer chain and can be employed as regulators. Compounds containing more than two active hydrogen atoms per molecule lead to the formation of branched polyureas.

The compounds which contain at least one active hydrogen atom per molecule are usually employed in a molar excess of active hydrogen atoms relative to the NCO groups of the polyisocyanate. The amount of component B which is introduced is usually in a molar excess, relative to the stoichiometric amount needed to convert the free isocyanate groups. Suitable polyesters, polyisocyanates, polyfunctional amines, and optional components that take part in the polyaddition or polycondensation, e.g. reaction, hydrophilic or hydrophobic components, protective colloids, stabilizing agent and further additives, are mentioned below.

Component (A): Poly(Ester-Urethane) Containing Isocyanate Groups

The term "polyurethane" comprises, in the context of this invention, not only polymers whose repeat units are bonded to one another via urethane groups but very generally polymers which can be obtained by reaction of at least one polyisocyanate with at least one compound exhibiting at least one group which is reactive with regard to isocyanate groups. These include polymers whose repeat units, in addition to urethane groups, are also connected by urea, allophanate, biuret, carbodiimide, amide, uretonimine, uretdione, isocyanurate or oxazolidone (oxazolidinone) groups (see, for example, Plastics Handbook, Saechtling, 26th edition, p. 491 seq., Carl Hanser Verlag, Munich, 1995). The term "polyurethane" comprises in particular polymers comprising urethane and/or urea groups.

The poly(ester-urethane) used according to the invention is preferably a reaction product of at least one polyester-polyol containing at least 2 hydroxyl groups (OH groups) with at least one polyisocyanate containing at least 2 isocyanate groups (NCO groups). The poly(ester-urethane) used according to the invention contains at least 2 isocyanate groups that are capable of reacting with complementary groups containing active hydrogen atoms.

The polyester-polyol typically has a OH functionality of greater than 1, preferably from 2 to 6, more preferably from 2 to 5, e.g. 2, 3 or 4.

In a special embodiment, the polyester-polyol is selected from aliphatic polyester-polyols.

The polyester-polyol preferably has a weight-average molecular weight of from 200 to 3000, more preferably from 205 to 2000, e.g. from 240 to 1240 g/mol.

The polyester-polyol typically has a hydroxyl value of from 20 to 800 mg KOH/g, preferably 30 to 600 mg KOH/g, more preferably 40 to 550 mg KOH/g.

The polyester-polyol typically has an acid number of from 0 to 15, preferably from 0 to 10, in particular 0 to 5.

The polyester-polyol typically has a viscosity at 60° C. of from 40 to 1100 mPa·s preferably from 100 to 500 mPa·s.

The polyester-polyol typically has at least 2, preferably 4, in particular 7 repeating units connected by ester groups.

Suitable polyesters-polyols include but not limited, for example, polyesters comprising in polymerized form trimethylene carbonate, ε-caprolactone, p-dioxanone, glycolide, lactide, 1,5-dioxepan-2-one, or the polyesters polybutylene adipate, polyethylene adipate, polyethylene terephthalate, and combinations thereof. In embodiments the polyester may comprise in polymerized form lactide, glycolide, ε-caprolactone, and/or combinations thereof.

Suitable polyester-polyols for the preparation of microcapsules according to the invention exhibit two or more than two (e.g., 3, 4, 5, 6, and the like) hydroxyl groups. In this connection, the hydroxyl groups can also be partially or completely replaced by mercapto groups.

Preferably, the polyester-polyol used for the preparation of the at least one poly(ester-urethane) A) contains in polymerized form
(a1) at least one polyol, and
(a2) at least one polycarboxylic acid, and/or
(a3) at least one hydroxycarboxylic acid.

More preferably, the polyester-polyol used for the preparation of the at least one poly(ester-urethane) A) contains in polymerized form at least one polyol (a1), and at least one hydroxycarboxylic acid (a3).

Suitable polyols (a1) are diols, polyols containing more than 2 OH groups and mixtures thereof. The term "polyols containing more than 2 OH groups" usually refers to polyols having at least 3 OH groups.

Suitable polyols containing more than 2 OH groups, and suitable polyols having at least 3 OH groups are triols and high molecular weight polyols (also called polymeric polyols), wherein triols are preferred. Preferred polyols (a1) are diols and triols, wherein triols are preferred. In particular polyols (a1) are selected from glycerol (propane-1,2,3-triol), butane-1,2,4-triol, n-pentane-1,2,5-triol, n-pentane-1,3,5-triol, n-hexane-1,2,6-triol, n-hexane-1,2,5-triol, (1,1,1)-trimethylolpropane (TMP) and trimethylolbutane.

Suitable diols are straight-chain and branched aliphatic and cycloaliphatic alcohols with generally approximately 2 to 30, preferably approximately 2 to 20, carbon atoms. These include 1,2-ethanediol, 1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol 1,2-hexanediol, 1,3-hexanediol, 1,4-hexanediol, 1,5-hexanediol, 1,6-hexanediol, 2,5-hexanediol, 1,2-heptanediol, 1,7-heptanediol, 1,2-octanediol, 1,8-octanediol, 1,2-nonanediol, 1,9-nonanediol, 1,2-decanediol, 1,10-decanediol, 1,12-dodecanediol, 2-methyl-1,3-propanediol, 2-methyl-2-butyl-1,3-propanediol, 2,2-dimethyl-1,3-propanediol, 2,2-dimethyl-1,4-butanediol, pinacol, 2-ethyl-2-butyl-1,3-propanediol, diethylene glycol, triethylene glycol, dipropylene glycol, tripropylene glycol, polyalkylene glycols, cyclopentanediols, cyclohexanediols, and the like.

Suitable triols are, e.g., glycerol (propane-1,2,3-triol), butane-1,2,4-triol, n-pentane-1,2,5-triol, n-pentane-1,3,5-triol, n-hexane-1,2,6-triol, n-hexane-1,2,5-triol, (1,1,1)-trimethylolpropane (TMP) and trimethylolbutane.

Suitable triols are furthermore the triesters of hydroxycarboxylic acids with trivalent alcohols. Preferably, in this connection, they are triglycerides of hydroxycarboxylic acids, such as, e.g., lactic acid, hydroxystearic acid and ricinoleic acid. Naturally occurring mixtures comprising hydroxycarboxylic acid triglycerides, in particular castor oil, are also suitable.

Suitable polyols of higher valency are, e.g., sugar alcohols and their derivatives, such as erythritol, pentaerythritol, dipentaerythritol, threitol, inositol and sorbitol. Reaction products of the polyols with alkylene oxides, such as ethylene oxide and/or propylene oxide, are also suitable.

Relatively high molecular weight polyols (also called herein polymeric polyols) with a number-average molecular weight in the range of approximately 400 to 6000 g/mol, preferably 500 to 4000 g/mol, can also be used. These include, e.g., polyalkylenglycoles (PEGs) such as polyethylene glycol (PEG) diol, and a copolymer diol of polyethylene glycol (PEG) diol and polypropylene glycol (PPG) diol or polybutylene glycol (PBG) diol. These furthermore include polytetrahydrofurandiols which can be obtained, e.g., by acid-catalyzed polymerization of tetrahydrofuran.

These furthermore include polylactonepolyols which are obtainable (preferably can be obtained) e.g. by ring-opening addition polymerization of a hydroxyl-terminated compound (e.g. diol or triol) and a monomer that includes a lactone ring (e.g., ε-caprolactone or β-methyl-δ-valerolactone).

These furthermore include polylactonediols which can be obtained, e.g., by polylactonediol obtained by ring-opening addition polymerization of a hydroxyl-terminated compound (e.g., polyol or polyester polyol) and a monomer that includes a lactone ring (e.g., ε-caprolactone or β-methyl-δ-valerolactone).

These furthermore include polyesterols based on aliphatic, cycloaliphatic and/or aromatic di-, tri- and/or polycarboxylic acids with di-, tri- and/or polyols, and also the polyesterols based on lactone. These furthermore include polyetherols which can be obtained, e.g., by polymerization of cyclic ethers or by reaction of alkylene oxides with an initiator molecule. These furthermore also include conventional polycarbonates with terminal hydroxyl groups known to a person skilled in the art which can be obtained by reaction of the diols described above or also bisphenols, such as bisphenol A, with phosgene or carbonic diesters. α,ω-Polyamidols, poly(methyl (meth)acrylate) α,ω-diols and/or poly(butyl (meth)acrylate α,ω-diols, such as, e.g., MD-1000 and BD-1000 from Goldschmidt, are also suitable.

In a preferred embodiment the poly(ester-urethane) A) is obtainable by reacting at least one polylactonpolyol containing at least 2 OH groups with at least one polyisocyanate containing at least 2 NCO groups. In other words, the polyester-polyol used for the preparation of the poly(ester-urethane) A) is a polylactonpolyol.

Preferably, the polylactonpolyol contains 2 or 3 OH groups. In particular, the polylactonpolyol is a polycaprolactonediol or a polycaprolactontriol.

Preferably, polylactonpolyol is a polycaprolactonediol or a polylactontriol having a number-average molecular weight of from 200 to 5000 g/mol, more preferably 250 to 3000 g/mol.

Preferably, the polyester-polyol is selected from compounds of the formulae (1), (2), (3), (4), (5) and mixtures thereof

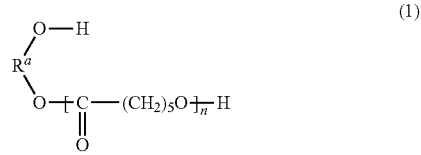

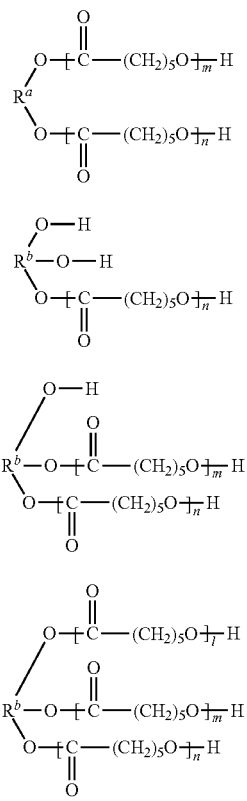

(2)

(3)

(4)

(5)

wherein $R^a$ is a divalent aliphatic or cycloaliphatic radical, $R^b$ is a trivalent aliphatic or cycloaliphatic radical l, m and n are independently an integer of 1 to 100, with the proviso that in the formula (1) n is an integer of 2 to 100, in the formula (2) n+m is an integer of 2 to 100, in the formula (3) n is an integer of 2 to 100, in the formula (4) n+m is an integer of 2 to 100, in the formula (5) n+m+l is an integer of 2 to 100.

Suitable radicals $R^a$ are linear or branched $C_1$-$C_{10}$-alkylene groups that are optionally interrupted by 1, 2, 3, 4 or 5 non-neighboring oxygen atoms and $C_3$-$C_{20}$-cycloaliphatic radicals having 3 to 10 ring carbon atoms.

Suitable radicals $R^b$ are linear or branched $C_1$-$C_{10}$-alkantriyl groups that are optionally interrupted by 1, 2, 3, 4 or 5 non-neighboring oxygen atoms.

Preferred radicals $R^a$ are methylene, 1,2-ethylene, 1,2-propylene, 1,3-propylene, 1,2-butylene, 1,3-butylene, 1,4-butylene, 1,1-dimethyl-1,2-ethylene, 1,2-dimethyl-1,2-ethylene, 1,5-pentylene, 1,6-hexylene, 1,8-octylene, 1,10-decylene, 1,12-dodecylene, —CH$_2$—O—CH$_2$—, —CH$_2$—CH$_2$—O—CH$_2$—CH$_2$— and —CH$_2$—CH$_2$—O—CH$_2$—CH$_2$—O—CH$_2$—CH$_2$—.

More preferred radicals $R^a$ are 1,2-ethylene, 1,2-propylene, 1,3-propylene, 1,2-butylene, 1,3-butylene, 1,4-butylene, —CH$_2$—CH$_2$—O—CH$_2$—CH$_2$— and —CH$_2$—CH$_2$—O—CH$_2$—CH$_2$—O—CH$_2$—CH$_2$—.

Preferred radicals $R^b$ are

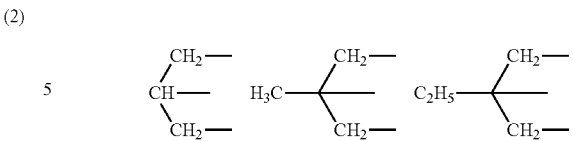

More preferably, the polyester-polyol is selected from compounds of the formulae (2), (5) and mixtures thereof, wherein compounds of the formulae (5) are in particular preferred.

In particular, the polyester-polyol is selected from compounds of the formulae (2), (5) and mixtures thereof (in particular from formula (5)), wherein $R^a$ is selected from linear or branched $C_1$-$C_{10}$-alkylene group and $C_3$-$C_{20}$-cycloaliphatic radicals having 3 to 10 ring carbon atoms, $R^b$ is a linear or branched $C_1$-$C_{10}$-alkantriyl group, l, m and n are independently an integer of 1 to 100, with the proviso that in the formula (2) n+m is an integer of 2 to 100, in the formula (5) n+m+l is an integer of 2 to 100.

In one preferred embodiment, the polyester-polyol containing at least 2 OH groups is obtainable (preferably it is obtained) by reaction of at least one diol and/or polyalkylenglycol with at least one polylacton, in particular the polyester-polyol containing at least 2 OH groups is obtained by reaction of diethylenglycol and poly-ε-caprolacton.

In another preferred embodiment, the polyester-polyol containing at least 2 OH groups is obtainable (preferably it is obtained) by reaction of at least one polyol having at least 3 OH groups with at least one polylacton, in particular the polyester-polyol containing at least 2 OH groups is obtained by reaction of trimethylolpropane and/or glycerol and poly-ε-caprolacton.

In another preferred embodiment, the polyester-polyol containing at least 2 OH groups is obtainable (preferably it is obtained) by reaction of at least one polyol having at least 3 OH groups selected from glycerol, butane-1,2,4-triol, n-pentane-1,2,5-triol, n-pentane-1,3,5-triol, n-hexane-1,2,6-triol, n-hexane-1,2,5-triol, (1,1,1)-trimethylolpropane and trimethylolbutane with at least one polylacton.

One embodiment relates to microcapsules as defined above and below, wherein the polyester-polyol containing at least 2 OH groups is obtainable (preferably it is obtained) by reaction of at least one diol and/or polyalkylenglycol with at least one polylacton.

Another embodiment relates to microcapsules as defined above and below, wherein the polyester-polyol containing at least 2 OH groups is obtainable (preferably it is obtained) by reaction of at least one polyol having at least 3 OH groups and/or polymeric polyol having at least 3 OH with at least one polylacton.

Suitable non-limiting examples of commercially available polyester-polyols are Caproper™ PD4-05 (a polycaprolactonediol), the LUPRAPHEN® brands available from BASF SE (e.g. Lupraphen 6601/3 a difunctional, aliphatic polyester-polyol) and (Tri-iso) Capa 3031 available from Perstorp.

One isocyanate group is supposed to react with a terminal hydroxyl group of the polyester-polyol and whilst the other isocyanate group of the diisocyanate is preserved. To avoid polymerization of high molecular weight chains, at least the mole equivalent of diisocyanate compared to hydroxyl groups has to be used in the reaction mixture. Once the functionalization is completed poly(ester-urethane)-diisocyanates are obtained as macromonomers.

The reaction progress is monitored by the frequent determination of the isocyanate content of the solution. The functionalization is complete after the conversion of 50% of the isocyanate groups. The isocyanate (NCO) content is declared in grams of NCO per 100 g reaction mixture.

Isocyanates are N-substituted organic derivatives (R—N=C=O) of isocyanic acid (HNCO) tautomeric in the free state with cyanic acid. Organic isocyanates are compounds in which the isocyanate group (—N=C=O) is bonded to an organic radical. Polyfunctional isocyanates are compounds with two or more (e.g. 3, 4, 5, etc.) isocyanate groups in the molecule.

Preferably, the polyisocyanate according to the invention comprises at least one difunctional isocyanate. In a special embodiment, the polyisocyanate is exclusively selected from difunctional isocyanates, the allophanates, isocyanurates, uretdiones or carbodiimides of difunctional isocyanates and mixtures thereof.

In general, suitable polyisocyanates are all aromatic, alicyclic and aliphatic polyisocyanates, provided they have at least two reactive isocyanate groups. Preferably, the polyisocyanate component has an average content of 2 to 4 NCO groups. Preference is given to using diisocyanates, i.e. esters of isocyanic acid with the general structure O=C=N—R'—N=C=O, where R' is an aliphatic, alicyclic or aromatic radical. Suitable polyisocyanates are chosen from compounds with 2 to 5 isocyanate groups, isocyanate prepolymers with an average number of from 2 to 5 isocyanate groups and mixtures thereof. These include, for example, aliphatic, cycloaliphatic and aromatic di-, tri- and higher polyisocyanates.

Preferably, the polyisocyanates comprise only a minor amount of compounds with aromatic rings. In particular, not more than 5 wt % of the polyisocyanates, based on the complete amount of the polyisocyanates, comprises an aromatic ring. In a special embodiment the polyisocyanate is selected only from aliphatic polyisocyanates. The term "aliphatic polyisocyanate" in the sense of the invention encompasses also non-aromatic cyclic polyisocyanates, e.g. isophorone diisocyanate.

Preferably, the polyisocyanate is selected from ethylene diisocyanate, tetramethylene diisocyanate, 1,5-pentamethylene diisocyanate, hexamethylene diisocyanate(1,6-diisocyanatohexane, HDI), octamethylene diisocyanate, decamethylene diisocyanate, dodecamethylene diisocyanate, tetradecamethylene diisocyanate,4-isocyanatomethyl-1,8-octamethylene diisocyanate, 1,6-diisocyanato-2,2,4-trimethylhexane, 1,6-diisocyanato-2,4,4-trimethylhexane, 2,3,3-trimethylhexamethylene diisocyanate, tetramethylhexane diisocyanate, lysine diisocyanate, isophorone diisocyanate (=3-Isocyanatmethyl-3,5,5-trimethylcyclohexylisocyanat, 1-Isocyanato-3-isocyanatomethyl-3,5,5-trimethylcyclohexan, IPDI), 1,4-cyclohexylene diisocyanate, 1,3-cyclohexylene diisocyanate, 1,2-cyclohexylene diisocyanate, 4,4'-di(isocyanatocyclohexyl)methane, or 2,4'-di(isocyanatocyclohexyl)methane, 1,3-bis(isocyanatomethyl)cyclohexane, 1,4-bis(isocyanatomethyl)cyclohexane, 1-methyl-2,4-diisocyanatocyclohexane, 1-methyl-2,6-diisocyanatocyclohexane, 1,3-phenylene diisocyanate, 1,4-phenylene diisocyanate, 2,4- and 2,6-toluylene diisocyanate and isomer mixtures thereof, 1,5-naphthylene diisocyanate, 2,4'- and 4,4'-diphenylmethane diisocyanate (MDI), mixtures of diphenylmethane diisocyanates and more highly polycyclic homologs of diphenylmethane diisocyanate (polymeric MDI), hydrogenated 4,4'-diphenylmethane diisocyanate (H12MDI), xylylene diisocyanate (XDI), tetramethylxylol diisocyanate (TMXDI), 4,4'-dibenzyl diisocyanate, 4,4'-diphenyldimethylmethane diisocyanate, di- and tetraalkyldiphenylmethandiisocyanates, triphenylmethane-4,4',4"-triisocyanate, dimer fatty acid diisocyanates, chlorinated and brominated diisocyanates, 4,4'-diisocyanatophenylperfluoroethane, tetramethoxybutane-1,4-diisocyanate, phosphorus-containing diisocyanates, sulfur-containing diisocyanares, anionically modified polyisocyanates, polyethylene oxide-containing isocyanate, oligomers of the aforementioned polyisocyanates that contain urethane, allophanate, isocyanurate, uretdione, carbodiimide or biuret groups, and mixtures thereof.

Suitable chlorinated and brominated polyisocyanates comprise polyisocyanates with reactive halogen atoms. Preferably, the chlorinated and brominated polyisocyanate is selected from 1-chloromethylphenyl 2,4-diisocyanate, 1-bromomethylphenyl 2,6-diisocyanate, 3,3-bischloromethyl ether 4,4'-diphenyldiisocyanate. Suitable sulfur-containing polyisocyanates are obtained, for example, by reacting 2 mol of hexamethylene diisocyanate with 1 mol of thiodiglycol or dihydroxydihexyl sulfide.

The polyisocyanate preferably comprises at least one aliphatic diisocyanate, selected from tetramethylene diisocyanate, 1,5-pentamethylene diisocyanate, hexamethylene diisocyanate(1,6-diisocyanatohexane), octamethylene diisocyanate, decamethylene diisocyanate, dodecamethylene diisocyanate, tetradecamethylene diisocyanate, lysine diisocyanate, trimethylhexane diisocyanate, tetramethylhexane diisocyanate, 1,4-diisocyanatocyclohexane, 1,3-diisocyanatocyclohexane, 1,2-diisocyanatocyclohexane, 4,4'-di(isocyanatocyclohexyl)methane, 2,4'-di(isocyanatocyclohexyl)methane, isophorone diisocyanate, 1,3-bis(isocyanatomethyl)cyclohexane, 1,4-bis(isocyanatomethyl)cyclohexane, 2,4-diisocyanato-1-methylcyclohexane and 2,6-diisocyanato-1-methylcyclohexane.

The polyisocyanate preferably comprises at least one polyisocyanate, selected from hexamethylene diisocyanate, tetramethylene diisocyanate, isophorone diisocyanate, dicyclohexylmethane-4,4'-diisocyanate, 2,4- and 2,6-toluylene diisocyanate and isomer mixtures thereof, 2,4'- and 4,4'-diphenylmethane diisocyanate, the biurets, allophanates and/or isocyanurates of the aforementioned polyisocyanates, anionically modified polyisocyanates, and mixtures thereof.

Preferably, polyisocyanates are selected from hexamethylene diisocyanate, tetramethylene diisocyanate, isophorone diisocyanate, dicyclohexylmethane-4,4'-diisocyanate, 2,4- and 2,6-toluylene diisocyanate and isomer mixtures thereof, 2,4'- and 4,4'-diphenylmethane diisocyanate and isomer mixtures thereof, the biurets, allophanates and/or isocyanurates of the afore-mentioned polyisocyanates or mixtures thereof.

In particular, the polyisocyanates are selected from hexamethylene diisocyanate, isophorone diisocyanate, dicyclohexylmethane-4,4'-diisocyanate, the isocyanurate of hexamethylene diisocyanate or mixtures thereof.

Especially, the polyisocyante is isophorone diisocyanate.

Component B

Component B) is at least one compound which comprises at least 2 terminal groups which are reactive towards isocyanate-groups, which are selected from OH, NHR, or SH, wherein R is selected from hydrogen, alkyl, cycloalkyl or aryl.

Suitable component B) are polyfunctional alcohols (such as diols, aminoalcohols, polymeric polyols having at least 3 OH groups) and polyfunctional amines (such as diamines, polymeric polyamines heaving at least 3 primary or secondary amino groups), and mixtures thereof.

Preferably, component B) comprises a polyfunctional amine (such as diamines, polymeric polyamines heaving at least 3 primary or secondary amino groups), and mixtures thereof.

More preferably, component B) comprises a polyfunctional amine selected from polyamidoamines (e.g. polylysine) and polyethyleneimines (e.g. diethylenetriamine, triethylenetetramine, tetraethylenepentamine, ethylenepropylenetriamine, trisaminopropylamine and higher polyethyleneimines).

The component B) may be selected from diols, diamines, aminoalcohols, polymeric polyols having at least 3 OH groups, polymeric polyamines heaving at least 3 primary or secondary amino groups and mixtures thereof.

The component B) is preferably selected from hexamethylene diamine, ethylenediamine, N ethylethylenediamine, N,N'-diethylethylenediamine, diethylenetriamine, tetraethylene pentamine, spermine, spermidine, polyaminosaccharides, polyvinylamines polyetheramines, polyesteramines, polyaminoacids and polyamidoamines and mixtures thereof.

Even more preference for component B) is given to hexamethylene diamine, ethylenediamine, N-ethylethylenediamine, N,N'-diethylethylenediamine, diethylenetriamine, tetraethylene pentamine, spermine, spermidine, polyvinylamines, polyetheramines, polyesteramines and polyamidoamines.

In the sense of the invention, the term polyfunctional alcohol denotes alcohols that comprise at least two groups capable of reacting with NCO groups, wherein at least one of the groups capable of reacting with NCO groups is a OH group. When the polyfunctional alcohol contains only one OH group, it will contain one or more additional functional groups that are capable of reacting with NCO groups in a polymerisation reaction. Suitable are in principle active hydrogen atom containing groups. The groups of the polyfunctional alcohol that are reactive toward NCO groups are preferably chosen from hydroxyl groups and primary and secondary amino groups.

Suitable polyfunctional alcohols according to the exhibit two or more than two (e.g., 3, 4, 5, 6, and the like) hydroxyl groups. In this connection, the hydroxyl groups can also be partially or completely replaced by mercapto groups.

Examples for polyfunctional alcohols are diols, triols, polyols of higher valency, and high molecular weight polyols.

Suitable diols are straight-chain and branched aliphatic and cycloaliphatic alcohols with generally approximately 2 to 30, preferably approximately 2 to 20, carbon atoms. These include 1,2-ethanediol, 1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol 1,2-hexanediol, 1,3-hexanediol, 1,4-hexanediol, 1,5-hexanediol, 1,6-hexanediol, 2,5-hexanediol, 1,2-heptanediol, 1,7-heptanediol, 1,2-octanediol, 1,8-octanediol, 1,2-nonanediol, 1,9-nonanediol, 1,2-decanediol, 1,10-decanediol, 1,12-dodecanediol, 2-methyl-1,3-propanediol, 2-methyl-2-butyl-1,3-propanediol, 2,2-dimethyl-1,3-propanediol, 2,2-dimethyl-1,4-butanediol, pinacol, 2-ethyl-2-butyl-1,3-propanediol, diethylene glycol, triethylene glycol, dipropylene glycol, tripropylene glycol, polyalkylene glycols, cyclopentanediols, cyclohexanediols, and the like.

Suitable triols are, e.g., glycerol, butane-1,2,4-triol, n-pentane-1,2,5-triol, n-pentane-1,3,5-triol, n-hexane-1,2,6-triol, n-hexane-1,2,5-triol, trimethylolpropane and trimethylolbutane. Suitable triols are furthermore the triesters of hydroxycarboxylic acids with trivalent alcohols. Preferably, in this connection, they are triglycerides of hydroxycarboxylic acids, such as, e.g., lactic acid, hydroxystearic acid and ricinoleic acid. Naturally occurring mixtures comprising hydroxycarboxylic acid triglycerides, in particular castor oil, are also suitable.

Suitable polyols of higher valency are, e.g., sugar alcohols and their derivatives, such as erythritol, pentaerythritol, dipentaerythritol, threitol, inositol and sorbitol. Reaction products of the polyols with alkylene oxides, such as ethylene oxide and/or propylene oxide, are also suitable.

Relatively high molecular weight polyols with a number-average molecular weight in the range of approximately 400 to 6000 g/mol, preferably 500 to 4000 g/mol, can also be used. These include, e.g., polyesterols based on aliphatic, cycloaliphatic and/or aromatic di-, tri- and/or polycarboxylic acids with di-, tri- and/or polyols, and also the polyesterols based on lactone. These furthermore include polyetherols which can be obtained, e.g., by polymerization of cyclic ethers or by reaction of alkylene oxides with an initiator molecule. These furthermore also include conventional polycarbonates with terminal hydroxyl groups known to a person skilled in the art which can be obtained by reaction of the diols described above or also bisphenols, such as bisphenol A, with phosgene or carbonic diesters. $\alpha,\omega$-Polyamidols, poly(methyl (meth)acrylate) $\alpha,\omega$-diols and/or poly(butyl (meth)acrylate $\alpha,\omega$-diols, such as, e.g., MD-1000 and BD-1000 from Goldschmidt, are also suitable.

Suitable as component B) are also polyfunctional amines. In the sense of the invention, the term polyfunctional amine denotes amines that comprise at least two groups capable of reacting with NCO groups, wherein at least one of the groups capable of reacting with NCO groups is a primary or secondary amino group. When the polyfunctional amine contains only one primary or secondary amino group, it will contain one or more additional functional groups that are capable of reacting with NCO groups in a polymerisation reaction. Suitable are in principle active hydrogen atom containing groups. The groups of the polyfunctional amines that are reactive toward NCO groups are preferably chosen from hydroxyl groups and primary and secondary amino groups.

The polyfunctional amine is preferably selected from diamines, aminoalcohols, polymeric polyamines, guanidines, melamines, urea, hydrazines and mixtures thereof. Preferred polyfunctional amine are selected from polymeric polyamines, wherein polyamidoamines and polyethyleneimines are more preferred.

Suitable diamines are, for example, 1,2-ethylenediamine, 1,3-propylenediamine, 1,4-diaminobutane, 1,5-diaminopentane (cadaverine), 1,6-diaminohexane, 1,3-diamino-1-methylpropane, 1,4-diaminocyclohexane, piperazin, N-ethylethylenediamine, N,N'-diethylethylenediamine and mixtures thereof.

Suitable amines which have at least two primary or secondary amino groups are, for example diethylenetriamine, tetraethylene pentamine, spermine, spermidine and mixtures thereof.

Suitable amino alcohols are, for example, 2-aminoethanol, 2-(N-methylamino)ethanol, 3-aminopropanol, 4-aminobutanol, 1-ethylaminobutan-2-ol, 2-amino-2-methyl-1-propanol, 4-methyl-4-aminopentan-2-ol, etc.

Suitable polymeric polyamines are in principle linear or branched polymers that have at least two primary or secondary amino groups. Additionally, these polymers can have tertiary amino groups in the polymer chain.

Preference is given to polymeric polyamines having a weight-average molecular weight of at least 300 g/mol.

More preferred are polymeric polyamines having a weight-average molecular weight of from 350 to 3000, in particular from 375 to 2500, especially from 400 to 2000, more especially from 500 to 1500. Furthermore, polymeric polyamines typically has at least 3, preferably 4, in particular 5 repeating units.

The polymeric polyamine is preferably selected from polyaminosaccharides, polyamidoamines, polyesteramines, polyetheramines, polyvinylamines, polyaminoacids, polyethyleneimines, and combinations thereof.

Preferably, the polymeric polyamine comprises a polyamidoamines, in particular polylysine. More preferably, the polymeric polyamine comprises polylysine which has a average molecular weight from of 300 to 4000 g/mol, preferably from 500 to 3000 g/mol.

In another preferred form, the polymeric polyamine comprises a polyethyleneimines (in particular diethylenetriamine, triethylenetetramine, tetraethylenepentamine, ethylenepropylenetriamine, trisaminopropylamine and higher polyethyleneimines), wherein polyethyleneimines may have a number-average molecular weight of at least 300 g/mol, preferably from 400 to 3000 or 450 to 2500 g/mol and in particular from 450 to 2000 g/mol.

Preferred polyesteramines are in the context of the present invention, very generally polymeric compounds exhibiting ester groups and amino groups in the chain, amino groups not being part of an amide group. In principle, at least divalent compounds exhibiting one amino group, preferably no longer available for a subsequent reaction, and at least two additional functional groups, capable of an addition or condensation reaction, can be used. These include, for example, N-alkyl-N-(hydroxyalkyl)aminoalkanecarboxylic acids and carboxylic acid derivatives, N,N-di(hydroxyalkyl) aminoalkanecarboxylic acids and carboxylic acid derivatives, N-alkyl-N-(aminoalkyl)aminoalkanecarboxylic acids and carboxylic acid derivatives, N,N-di(aminoalkyl)aminoalkanecarboxylic acids and carboxylic acid derivatives, and the like. In addition to these monomers, the polyesteramines used according to the invention can comprise additional polyfunctional compounds incorporated exhibiting two or more than two (e.g., 3, 4, 5, 6, and the like) functional groups. These include the above-described polycarboxylic acids, polyfunctional amines, polyfunctional alcohols and polyfunctional aminoalcohols, reference to which is made here in their entirety.

Preferred polyamidoamines are dendrimer which is made of repetitively branched subunits of amide and amine functionality. Preferred polyamidoamines are polylysine, which is homopolymers from lysine. It is prepared from amino acid lysine, which contains two amino groups, one at the α-carbon and one at the ε-carbon. Either can be the location of polymerization, resulting in α-polylysine or ε-polylysine. Preference is given to polylysine which have a average molecular weight from of 300 to 4000 g/mol, preferably from 400 to 3000 g/mol, more preferably, 500 to 1500 g/mol. Furthermore, polylysine according to the invention has at least 3, preferably 4, in particular 5 repeating units.

Preferred polyaminosaccharides are sugar molecule in which a hydroxyl group has been replaced with an amine group. Preferred are chitosan composed of randomly distributed β-(1-4)-linked D-glucosamine (deacetylated unit) and N-acetyl-D-glucosamine (acetylated unit).

Preferred polyvinylamines (polyaminoethylene) are known products obtained by homo- or copolymerization of N-vinylformamide followed by partial or complete hydrolysis.

Preferred polyetheramines are the reaction products of at least one polyol with at least one $C_2$-$C_{18}$ alkylene oxide, to form an alkoxylated polyol and aminating the alkoxylated polyol with ammonia.

Preferred polyamino acids usually consist of repeating units of amino acids, wherein the homopolyamino acid is made from up of a single amino acid as a repeating unit, and the co-polyamino acid is a polymer made from at least two or more different amino acids as repeating units. Polyamino acids contain both an amino and a carboxylic acid functional group. Preferred polyamino acids are selected from the group consisting of poly-D,L-ornithine, poly-D,L-homoarginine, poly-D,L-arginine, poly-D,L-glutamic acid, poly-D,L-glutamic acid, poly-D,L-glutamic acid, poly-D,L-aspartic acid.

Preferred are also polyethyleneimines, which are selected from the group consisting of diethylenetriamine, triethylenetetramine, tetraethylenepentamine, ethylenepropylenetriamine, trisaminopropylamine and higher polyethyleneimines. Preferably the polyethyleneimines have a number-average molecular weight of at least 300 g/mol, preferably from 400 to 3000 or 450 to 2500 g/mol and in particular from 450 to 2000 g/mol. In a preferred embodiment, the polymeric polyamine is selected from polyethyleneimines having a weight average molecular weight of at least 300 g/mol. Suitable polyethylenimines contain the following repeat units

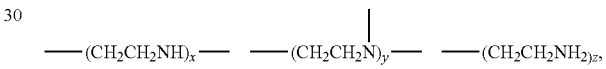

wherein
x is from 8 to 1500, preferably from 10 to 1000;
y is from 0 to 10, preferably from 0 to 5, especially 0;
z is 2+y.

Preferred polyethyleneimines are linear polyethyleneimines, wherein x is from 8 to 1500, y is 0 and z is 2. Preferred commercially available polyethylenimines are sold by BASF SE under the trademark Lupasol™ and the Jeffamine trademarks from Huntsman, particularly Lupasol™ PR8515.

If the core essentially contains only hydrophilic components, preference is given polyaminosaccharides, polyamidoamines, polyesteramines, polyetheramines, polyvinylamines and combinations thereof, preferably, polyamidoamine, in particular polylysine.

In a special embodiment of the invention the polymeric shell material shows biodegradability.

In a preferred embodiment for providing a biodegradable polymeric shell material the poly(ester-urethane) A) is prepared by reacting at least one polycaprolactonediol or a polylactonetriol having a number-average molecular weight of from 250 to 3000 g/mol with at least one polyisocyanate containing at least 2 NCO groups.

Core Material

Suitable hydrophilic components are mentioned in detail below. The term "the core essentially contains only hydrophilic components" usually means that the core contains at least 80 wt %, preferably at least 90 wt %, more preferably at least 95 wt %, and in particular at least 98 wt % of the hydrophilic components.

In the sense of the invention, the term "hydrophilic component" is understood in a broad sense. It encompasses a single hydrophilic component, a mixture comprising at least two hydrophilic components and a solution of at least one hydrophilic solid compound in a liquid hydrophilic compound. The hydrophilic compound must have greater affinity to the hydrophilic phase than to the hydrophobic phase. This is generally ensured if the compound has a solubility in the hydrophilic solvent (such as water) at room temperature of at least 1 g/l. The hydrophilic compound (e.g. the pesticide) preferably have a solubility in the hydrophilic solvent (such as water) of ≥20 g/l. Furthermore, hydrophilic components are water as well as aqueous solutions of water soluble compounds (e.g. pesticides).

In another form the hydrophilic components have a solubility in water of at least 1 g/l at room temperature (e.g. 20° C.), more preferably of at least 20 g/l, and in particular at least 50 g/l.

Generally, water soluble compounds are selected from the group consisting of organic acids and salts thereof; inorganic acids; inorganic bases; salts of the inorganic acids, e.g. sodium chlorid or sodium nitrate; watersoluble dyes; agrochemicals, e.g. Dicamba®; flavour additives; pharmaceutical active ingredients; cosmetically ingredients; fertilizer. Preferably the hydrophilic component is selected from water and water soluble compounds of organic acids, like acetic acid, formic acid, propionic acid, methansulfonic acid and salts thereof; inorganic acids, like phosphoric acid, hydrochloric acid and salts thereof; inorganic salts, like sodium silicate.

In a special embodiment of the invention, the microcapsules contain substantially no solvent in the core.

In a special embodiment of the invention, the microcapsules contain substantially no solvent in the core. According to the process of the invention, it is possible to prepare a microcapsule composition, wherein the encapsulated cores are composed entirely of hydrophilic components and no solvents. Solvent-free encapsulated hydrophilic components may be employed, in particular, when the hydrophilic components making up the core material are liquid under the conditions used for the preparation of the microcapsules.

The microcapsules contain one or more hydrophilic components (e.g. the pesticide). Preferably, the amount of the hydrophilic components (e.g. the pesticide) is in a range of from 5 to 97% by weight, more preferably 10 to 95% by weight, in particular 25 to 93% by weight, based on the total weight of the microcapsules. In a special embodiment, the amount of the hydrophilic components is in a range of from 70 to 98% by weight, based on the total weight of the microcapsules.

Advantageously, a large amount of hydrophilic components can be encapsulated in the microcapsules of the invention despite the relatively low shell weight. Preferably, the ratio of the total weight of the hydrophilic components to total weight of the shell material is in a range of from 60% to 95% by weight, more preferably 75% to 80% by weight, and more particularly 80% to 88% by weight.

In another form the core-shell ratio (w/w) of the microcapsules is 20:1 to 1:10, preferably 10:1 to 5:1 and in particular 4:1 to 3:1. In a preferred form the core-shell ratio (w/w) of the microcapsules is 20:1 to 1:1, preferably 13:1 to 2:1 and in particular 10:1 to 3:1.

The core-shell weight ratio may be obtained by weighing an amount of capsules that have been previously washed with water and separated by filtration. The core is then extracted by solvent extraction techniques to give a core weight. The shell weight is obtained from simple mass balance taking into account the initial amount of encapsulating materials in weight %.

Hydrophilic components that are used can be various organic substances. In particular, the hydrophilic component is selected from active ingredients and auxiliaries for cosmetics (e.g. hair and skin cosmetics), pharmaceuticals, hygiene compositions, detergents, cleaning agents, textile treatment compositions, etc., compositions used for industrial or institutional or hospital applications, material protection compositions or plant protection compositions.

Active ingredients are substances which generally develop an effect even at low concentration, e.g. a cosmetic effect on skin and/or hair, a pharmacological effect in an organism, a plant protecting effect, a cleaning and/or disinfecting effect, a modification of a textile substance, e.g. a crease-free finishing, and effect substances which impart a certain property to living things or inanimate substrates, for example colors for make-up, mascara, etc.

Preferably, the hydrophilic component is selected from UV-filters, organic compounds biocides, dyes, emollients, vitamins, cosmetically active ingredients, pharmaceutically active ingredients, cosmetically and pharmaceutically acceptable auxiliaries, detergents, anti-oxidants, perfumes and fragrances or mixtures thereof.

In one embodiment the hydrophilic component of the microcapsule or microcapsule dispersion as defined above is selected from UV-filters, organic compounds, biocides, dyes, emollients, vitamins, cosmetically active ingredients, pharmaceutically ingredient, detergent composition, anti-oxidant agents, fragrances or mixtures thereof.

A further class of hydrophilic components that can be encapsulated are UV filters. Preferably, the hydrophilic components comprise at least one UV filters capable to dissolve the component (B). More preferably, these UV-filters are capable to dissolve the component (B) without extraneous solvents and/or auxiliaries. Should an UV filter not ensure adequate solubility of the polyisocyanates, there is the option of overcoming this disadvantage by using suitable solubility promoters.

A further class of hydrophilic components that can be encapsulated are biocides.

Preferably, the hydrophilic components comprise at least one biocide capable to dissolve component (B). More preferably, these biocides are capable to dissolve the component (B) without extraneous solvents and/or auxiliaries. Should a biocide not ensure adequate solubility of the component (B), there is the option of overcoming this disadvantage by using suitable solubility promoters.

A biocide may be a chemical substance, capable of killing different forms of living organisms used in fields, such as medicine, agriculture, forestry, and mosquito control. Usually, biocides are divided into two sub-groups:

- pesticides which includes fungicides, herbicides, insecticides, algicides, moluscicides, miticides and rodenticides, and
- antimicrobials which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

In a preferred form the hydrophobic component comprises a pesticide and optionally water. The pesticide may be dissolved in water.

In one form suitable pesticides include fungicides, herbicides, insecticides, algicides, moluscicides, miticides and rodenticides. In another form the term pesticide usually refers to at least one active substance selected from the group of the fungicides, insecticides, nematicides, herbicides, safeners, biopesticides and/or growth regulators. Preferred pesticides are fungicides, insecticides, herbicides and growth regulators. Especially preferred pesticides are herbicides. Mixtures of pesticides of two or more of the abovementioned classes may also be used. The skilled worker is familiar with such pesticides, which can be found, for example, in the Pesticide Manual, 17th Ed. (2015), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxy-propionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

A further class of hydrophilic components that can be encapsulated are emollients. Preferably, the hydrophilic components comprise at least one emollient capable to dissolve the component (B). More preferably, these emollients are capable to dissolve the component (B) without extraneous solvents and/or auxiliaries. Should an emollient not ensure adequate solubility of the component (B), there is the option of overcoming this disadvantage by using suitable solubility promoters. An emollient is a material that softens, soothes, supplies, coats, lubricates, moisturizes, or cleanses the skin. An emollient typically accomplishes several of these objectives such as soothing, moisturizing, and lubricating the skin.

A further class of hydrophilic components that can be encapsulated are dyes. Preferably, the hydrophilic components comprise at least one dye capable to dissolve the component (B). More preferably, these dyes are capable to dissolve the component (B) without extraneous solvents and/or auxiliaries. Should an dye not ensure adequate solubility of the component (B), there is the option of overcoming this disadvantage by using suitable solubility promoters. Preferred dyes according to the invention are dyes suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

A further class of hydrophilic components that can be encapsulated are cosmetically active ingredients. Preferably, the hydrophilic components comprise at least one cosmetically active ingredient capable to dissolve the component (B). More preferably, these cosmetically active ingredients are capable to dissolve the component (B) without extraneous solvents and/or auxiliaries. Should an cosmetically active ingredients not ensure adequate solubility of the component (B), there is the option of overcoming this disadvantage by using suitable solubility promoters. Suitable cosmetically active ingredients are, for example, skin and hair pigmentation agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinizing substances, active ingredients which have an antioxidative effect and/or free-radical scavenging effect, skin-moisturizing or -humectant substances, refatting active ingredients, deodorizing active ingredients, sebostatic active ingredients, plant extracts, antierythimatous or antiallergic active ingredients and mixtures thereof.

A further class of hydrophilic components that can be encapsulated are pharmaceutically ingredients. Preferably, the hydrophilic components comprise at least one pharmaceutically ingredient capable to dissolve the compound (B). More preferably, these pharmaceutically ingredients are capable to dissolve the component (B) without extraneous solvents and/or auxiliaries. Should a pharmaceutically ingredient not ensure adequate solubility of the polyisocyanates, there is the option of overcoming this disadvantage by using suitable solubility promoters. In principle, all pharmaceutical active substances and prodrugs are suitable for the use of the hydrophilic components according to the invention. These include benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, antiparkinsonians and other antihyperkinetic agents, ophthalmics, neuropathy preparations, calcium metabolism regulators, muscle relaxants, narcotics, antilipemics, hepatic therapeutic agents, coronary agents, cardiacs, immunotherapeutics, regulatory peptides and their inhibitors, hypnotics, sedatives, gynecological agents, antigouts, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta-receptor blockers, calcium antagonists, ACE inhibitors, antiarteriosclerotics, antiinflammatories, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents. Examples of suitable pharmaceutical active substances are in particular the active substances mentioned in paragraphs 0105 to 0131 of US 2003/0157170.

The hydrophilic component preferably comprises a pharmaceutically acceptable auxiliary. Of pharmaceutical acceptability are the auxiliaries that are known for use in the field of pharmacy, food technology and related fields, in particular the auxiliaries listed in relevant pharmacopoeia (e.g. DAB, Ph. Eur., BP, NF), as well as other auxiliaries whose properties do not preclude a physiological use. Suitable cosmetically and pharmaceutically acceptable auxiliaries are also described in Fiedler, H. P. Lexikon der Hilfsstoffe für Pharmazie, Kosmetik and angrenzende Gebiete [Lexicon of the auxiliaries for pharmacy, cosmetics and related fields], 4th edition, Aulendorf: ECV-Editio-Kantor-Verlag, 1996.

A further class of hydrophilic components that can be encapsulated are compositions used for industrial or institutional or hospital applications. Preferably, the hydrophilic components comprise at least one composition used for industrial or institutional or hospital applications capable to dissolve the component (B). More preferably, these are compositions used for industrial or institutional or hospital applications are capable to dissolve the component (B) without extraneous solvents and/or auxiliaries. Should a composition used for industrial or institutional or hospital applications not ensure adequate solubility of the component (B), there is the option of overcoming this disadvantage by using suitable solubility promoters. Suitable compositions used for industrial or institutional or hospital applications are, for example, chelants of heavy metal and hardness ions (builders), scale inhibiting agents, corrosion inhibiting agents, deflocculating/dispensing agents, stain removal agents, bleach stabilizing agents, protecting agents of peroxygen labile ingredients, photobleaching enhancing agents, thickener/viscosity modifying agents, crystal growth modification agents, sludge modification agents, surface modification agents, processing aids, electrolyte, hydrolytic stability agents, alkalinity agents and the like. The lipophilic components are compounds which are also useful for certain industrial applications, such as acid cleaners, aluminum etching, boiler cleaning, water treatment, bottle washing, cement modification, dairy cleaners, desalination, electrochemical machining, electroplating, metal finishing, paper mill evaporations, oil field water treatment, paper pulp bleaching, pigment dispersion, trace metal carrier for fertilizers, irrigation, circuit cleaning and the like.

A further class of hydrophilic components that can be encapsulated are textile treatment compositions. Preferably, the hydrophilic components comprise at least one textile treatment composition capable to dissolve the component (B). More preferably, these textile treatment compositions are capable to dissolve the component (B) without extraneous solvents and/or auxiliaries. Should a textile treatment composition not ensure adequate solubility of the component (B), there is the option of overcoming this disadvantage by using suitable solubility promoters. Suitable textile treatment compositions are softening compositions, such as liquid fabric softeners, fabric softening rinses, fabric softening sheets, tissue papers, paper towels, facial tissues, sanitary tissues, toilet paper and the like.

A further class of hydrophilic components that can be encapsulated are vitamins. Suitable water-soluble vitamins and provitamins are e.g. vitamin A, vitamin A acetate, vitamin D, vitamin E, tocopherol derivatives, such as tocopherol acetate and vitamin K.

A further class of hydrophilic components that can be encapsulated are anti-oxidants. Suitable anti-oxidants includes, for example: alkylated monophenols, alkylthiomethylphenols, hydroquinones and alkylated hydroquinones, tocopherols, hydroxylated thiodiphenyl ether, alkylidenebisphenols, benzyl compounds, hydroxybenzylated malonates, hydroxybenzyl aromatics, triazine compounds, benzylphosphonates, acylaminophenols, esters of β-(3,5-di-tert-butyl-4-hydroxyphenyl)propionic acid with monohydric or polyhydric alcohols, esters of β-(5-tert-butyl-4-hydroxy-3-methylphenyl)propionic acid with monohydric or polyhydric alcohols, esters of β-(3,5-dicyclohexyl-4-hydroxyphenyl)propionic acid with monohydric or polyhydric alcohols, esters of 3,5-di-tert-butyl-4-hydroxyphenylacetic acid with monohydric or polyhydric alcohols, amides of β-(3,5-di-tert-butyl-4-hydroxyphenyl)propionic acid, ascorbic acid (vitamin C) or aminic antioxidants.

A further class of hydrophilic components that can be encapsulated are perfumes and fragrances. Suitable fragrances employed according the present invention are conventional ones known in the art. Suitable perfume compounds and compositions can be found in the art including U.S. Pat. No. 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; U.S. Pat. No. 4,152,272, Young, issued May 1, 1979; U.S. Pat. No. 5,378,468 Suffis et al.; U.S. Pat. No. 5,081,000 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al., issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/38528 published Dec. 5, 1996; WO 96/14827 published May 23, 1996; WO 95/04809 published Feb. 16, 1995; and WO 95/16660 published Jun. 22, 1995; all of said U.S. patents and U.S. references being incorporated herein by reference. In addition, P. M. Muller, D. Lamparsky Perfumes Art, Science, & Technology Blackie Academic & Professional, (New York, 1994) is included herein by reference. Fragrances can be classified according to their volatility. The highly volatile, low boiling, perfume ingredients typically have boiling points of about 250° C. or lower. The moderately volatile perfume ingredients are those having boiling of from about 250° C. to about 300° C. The less volatile, high boiling, perfume ingredients are those having boiling points of about 300° C. or higher. Many of the perfume ingredients as discussed hereinafter along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

The present invention relates also to a process for the preparation of microcapsules or a dispersion of the microcapsules as defined above.

Embodiment (1): The Process for the Preparation of a Microcapsule Dispersion, Wherein the Microcapsules are Defined Above and the Core Essentially Contains Only a Hydrophilic Components Comprising the Following Steps a) providing a premix (Ia) comprising the hydrophilic component(s) to be encapsulated (Ca), optionally a hydrophilic medium that is liquid at 20° C. and 1023 mbar different from (Ca), and at least one component (B) as defined above, and
b) mixing the premix (Ia) provided in step a) with an hydrophobic medium (IIa) comprising at least one hydrophobic protective colloid, at least one component (A) as defined above, and reacting the resulting mixture to form microcapsules dispersed in the hydrophobic medium (IIa).

The capsule core comprises at least one hydrophilic component as solid and/or, depending on the preparation, as solution in the hydrophobic medium (e.g. a hydrophilic solvent). Preferred capsule cores are solutions of the water-soluble compound (e.g. the pesticide).

The basic principle of capsule formation is usually that the hydrophilic component dissolved in the hydrophilic medium and which is the hydrophilic phase of a water-in-oil emulsion becomes insoluble over the course of the condensation and migrates to the interface of the hydrophobic phase, where it forms the capsule wall.

Hydrophilic medium (e.g. a hydrophilic solvent) is to be understood as meaning either water or those aqueous solutions which, apart from water, comprise up to 20% by weight of a water-miscible organic solvent, such as $C_1$- to $C_4$-alkanols, in particular methanol, ethanol, isopropanol or a cyclic ether, such as tetrahydrofuran. Suitable hydrophilic media are also ethylene glycol, glycerol, polyethylene glycols and butylene glycol, and their mixtures. Preferred hydrophilic media are water and mixtures of these solvents with water.

Preferrably the hydrophylic component (Ca) is soluble in the hydrophilic medium.

The hydrophobic medium (IIa) usually forms the hydrophobic phase. Suitable hydrophobic phase of the water-in-oil emulsion are solvents with only limited miscibility with water so that phase separation takes place. Hydrophobic solvents which may be used are virtually all water-immiscible liquids which do not interfere with the polycondensation, i.e. are inert. Solvents suitable according to the invention are preferably solvents with a solubility in water at 20° C., and 1023 mbar of <1 g/L, preferably <0.5 g/L. Preference is given here to using aliphatic and aromatic hydrocarbons or their mixtures. Suitable aliphatic hydrocarbons are, for example, pentane, hexane, heptane, octane, nonane, decane, cyclohexane, decalin, methylcyclohexane, isooctane and ethylcyclohexane. Suitable aromatic hydrocarbons are, for example, benzene, toluene, xylene and isopropylbenzene. In addition, it is also possible to use halogenated hydrocarbons, such as tetrachloroethane, hexachloroethane, trichloroethane and chlorobenzene. In addition, aliphatic esters, such as ethyl acetate, are suitable. Preference is given to using aliphatic hydrocarbons and, in particular, cyclohexane. Preference is given to solvents whose boiling point is ≤120° C. since these solvents can be removed advantageously if the microcapsules are dried.

In order to obtain a stable water-in-oil emulsion, surface-active substances such as protective colloids are required. Such protective colloids are known from processes for inverse suspension polymerization, cf. DE-A-1081228 and DE-A-3709921. Use is usually made of protective colloids which dissolve in the hydrophobic phase.

Examples of suitable hydrophobic protective colloids are alkylated polyvinylpyrrolidones, ethylene oxide/propylene oxide copolymers and ethoxylated fatty alcohols (EO degree=3 to 50, alkyl radical: $C_8$ to $C_{36}$).

Preference is given to hydrophobic protective colloids based on copolymers of monoethylenically unsaturated carboxylic acids with monovinylaromatic comonomers, e.g. styrene, esters of (meth)acrylic acid, vinyl acetate, acrylamide, methacrylamide, acrylonitrile and hydroxyalkyl (meth) acrylates. Protective colloids which have proven particularly advantageous are those obtainable by grafting polymers P) comprising
a) 40 to 95% by weight of monovinylaromatic monomers,
b) 5 to 60% by weight of monoethylenically unsaturated carboxylic acids having 3 to 6 carbon atoms, maleic anhydride and/or itaconic anhydride and
c) 0 to 20% by weight of other monoethylenically unsaturated monomers, with the proviso that the sum of the percentages by weight (a) to (c) is always 100 and the polymers (P) have a molecular weight (number-average) of from 500 to 20 000, with monomer mixtures being more preferred comprising
a) 70 to 100% by weight of acrylic esters and/or methacrylic esters of monohydric alcohols containing 1 to 20 carbon atoms,
b) 0 to 15% by weight of monoethylenically unsaturated carboxylic acids having 3 to 6 carbon atoms, maleic anhydride and/or itaconic anhydride,
c) 0 to 10% by weight of acrylic monoesters and/or methacrylic monoesters of at least dihydric alcohols,
d) 0 to 15% by weight of monovinylaromatic monomers and
e) 0 to 7.5% by weight of acrylamide and/or methacrylamide with the proviso that the sum of the percentages by weight a) to e) is always 100, where the monomers are used in an amount of from 97.5 to 50% by weight, based on the mixture of polymer (P) and monomers. Such graft polymers and processes for their preparation are known from DE-A-3709921.

The polymers P) are usually copolymers of monovinylaromatic monomers with an ethylenically unsaturated carboxylic acid or an anhydride of a monoethylenically unsaturated carboxylic acid.

Suitable as component a) of the polymers P) are monovinylaromatic monomers, e.g. styrene, α-methylstyrene, α-alkylstyrenes having 2 to 6 carbon atoms in the alkyl radical, which may be straight-chain and/or branched, e.g. α-isobutylstyrene. Also suitable are vinylaromatics which, apart from the vinyl group on the aromatic core, carry a $C_1$- to $C_8$-alkyl group, e.g. vinyltoluene, tert-butylstyrene, halogenated styrenes, core (alkyl)-substituted α-alkylstyrenes having 1 to 8 carbon atoms in the core alkyl radical and having 1 to 6 carbon atoms in the α-alkyl radical, e.g. para-tert-butyl-α-methylstyrene. Preference is given to using styrene from this group of monomers. Components a) in particular styrene are preferably involved in an amount of 60 to 95% by weight in the construction of the polymer P).

The monomers of group b) include monoethylenically unsaturated carboxylic acids having 3 to 6 carbon atoms and/or anhydrides thereof, e.g. acrylic acid, methacrylic acid, ethacrylic acid, maleic acid, fumaric acid, itaconic acid, maleic anhydride, itaconic anhydride, vinyllactic acid, vinylphosphonic acid and vinylsulfonic acid. These monomers are either used alone or in a mixture. From this group of monomers, preference is given to using acrylic acid, methacrylic acid, maleic anhydride and itaconic anhydride. The monomers of this group are preferably involved in an amount of 5 to 40% by weight in the construction of the polymers P).

Apart from the monomers of groups a) and b), up to 20% by weight of other monoethylenically unsaturated monomers c) may also be present in the polymers P) in polymerized form. This group of monomers includes, for example, the esters of acrylic acid, methacrylic acid and/or ethacrylic acid which are derived from alcohols having 1 to 12 carbon atoms, e.g. methyl acrylate, methyl methacrylate, tert-butylcyclohexyl acrylate, tert-butylcyclohexyl methacrylate, cyclohexyl acrylate, cyclohexyl methacrylate, tert-butyl acrylate, tert-butyl methacrylate, n-butyl acrylate, n-butyl methacrylate, isobutyl acrylate, isobutyl methacrylate, 2-ethylhexyl acrylate, 2-ethylhexyl methacrylate, and vinyl esters of saturated aliphatic carboxylic acids which contain 2 to 10 carbon atoms, e.g. vinyl acetate, vinyl propionate, vinyl laurate, vinyl butyrate and vinyl stearate. Another group of monomers are the amides of methacrylic acid, acrylic acid and ethacrylic acid. Here, these may, for example, be methacrylamide or acrylamide, and N-substituted amides, such as N-tert-butylmethacrylamide or N-tert-butylacrylamide. A further class of monomers which may be involved in the construction of the polymer P) are acrylonitrile and methacrylonitrile. The monomers of the group of c) can either be incorporated by polymerization into the copolymer P-1) alone or in a mixture in amounts up to 20% by weight. The sum of the percentages a), b) and c) is 100 in each case.

The polymers P) have a molecular weight (number-average) of from 500 to 20000 and hydrogenation iodine numbers (in accordance with DIN 53241) of from 1.3 to 51, preferably 2.5 to 25.4. It is particularly preferred to use polymers P) whose hydrogenation iodine numbers are 5.1 to 16.9. The average molecular weight (number-average) of the polymers P) is preferably 1 000 to 10 000. Preference is given to using those polymers P) which are sparingly soluble in aliphatic hydrocarbons with a boiling range from 50 to 150° C.

Such polymers are known. They are prepared, for example, by homo- or copolymerization of the monomers a) to c) without diluent at 180 to 400° C., preferably 200 to 300° C. Particular preference is given to continuous bulk polymerization of the monomers which is carried out in the given temperature range and, in particular, at 200 to 260° C. and at pressures of from 1 to 100 bar, preferably 20 to 50 bar, in the absence of polymerization initiators or else in the presence of polymerization initiators and polymerization inhibitors. Such processes are described, for example, in DE-A-3026831, DE-A-3046476, U.S. Pat. No. 4,042,768 and WO 82/2387.

The polymers P) serve as graft base for the preparation of the protective colloids. For the preparation of the graft polymers, the procedure generally involves adding some of the polymerization initiator and some of a monomer mixture (e.g. comprising the monomers of group f, g, h, i, and j) to a solution or dispersion of the polymers P) in an aliphatic and/or aromatic hydrocarbon-preference is given to using the same solvents which are subsequently used in the preparation of the microcapsules as hydrophobic inert solvents- and heating to an elevated temperature and, after the polymerization has started, adding the remaining monomers and the polymerization initiator.

The monomers of group f) used are acrylic esters and/or methacrylic esters of monohydric alcohols containing 1 to 20 carbon atoms. Examples of this group of monomers are methyl acrylate, methyl methacrylate, ethyl acrylate, ethyl methacrylate, propyl acrylate, isopropyl acrylate, propyl methacrylate, n-butyl acrylate, sec-butyl acrylate, tert-butyl acrylate, tert-butyl methacrylate, sec-butyl methacrylate, n-butyl methacrylate, tert-butylcyclohexyl acrylate, tert-butylcyclohexyl methacrylate, cyclohexyl acrylate, 2-ethylhexyl acrylate, 2-ethylhexyl methacrylate and lauryl acrylate. It is also possible to use the esters of ethacrylic acid which are derived from monohydric alcohols having 1 to 12 carbon atoms. From this group of monomers, preference is given to using acrylic esters and/or methacrylic esters of monohydric alcohols containing 3 to 6 carbon atoms. Very particular preference is given to the use of tert-butyl acrylate, n-butyl acrylate and isobutyl acrylate or mixtures thereof in an amount of from 85 to 98% by weight, based on the monomer mixture which is grafted onto the polymer P). The monomers of group f) are generally used in an amount of from 70 to 100% by weight, based on the monomers to be grafted. In the case of only a slight modification, the amount of monomers of group f) is 92.5 to 100% by weight.

Suitable monomers of group g) are monoethylenically unsaturated carboxylic acids having 3 to 6 carbon atoms and/or anhydrides thereof. This group of monomers corresponds to the monomers of group b) of polymers P). Specifically, these are, for example, acrylic acid, methacrylic acid, ethacrylic acid, fumaric acid, the anhydrides of said carboxylic acids and maleic anhydride. This group of monomers is optionally co-used in the preparation of the graft polymers and is present in an amount of from 0 to 15% by weight in the monomer mixture which is grafted onto the polymer P). From this group of monomers, preference is given to using acrylic acid, methacrylic acid, maleic anhydride or itaconic anhydride in an amount of from 0 to 7.5% by weight, based on the monomers.

A further group h) of monomers which can be grafted onto the polymer P) which may be mentioned are acrylic monoesters and/or methacrylic monoesters of at least dihydric alcohols. These include, for example, hydroxyethyl acrylate, hydroxyethyl methacrylate, hydroxypropyl acrylate, hydroxypropyl methacrylate, hydroxybutyl acrylate and hydroxybutyl methacrylate. This group of monomers is optionally co-used in a monomer mixture in an amount up to 10% by weight.

A further modification of the polymers P) can take place by grafting on monomers of group i). These monomers include monovinylaromatic compounds which may be present in an amount up to 15% by weight, preferably 1 to 7.5% by weight, in the monomer mixture. These monomers are identical to the monomers of group a) of polymers P). From this group of monomers, preference is given to using styrene.

A further modification can take place if the mixture of the monomers which are grafted onto the polymers P) comprises, as monomers j), optionally up to 7.5% by weight of acrylamide and/or methacrylamide.

The sum of the percentages by weight of the monomers of group g) to j) is always 100. The monomers g) to j) are used in an amount of from 97.5 to 50% by weight, preferably 90 to 75% by weight, based on the mixture of polymer P) and the monomers a) to e), for the preparation of the graft polymers.

The graft polymerization is generally carried out at temperatures up to 50° C., preferably from 50 to 150° C., preferably 60 to 120° C., in the presence of polymerization initiators, which are generally used in an amount of from 0.01 to 6% by weight, preferably 0.1 to 4% by weight, based on the weight of the polymers A) and the monomer mixture. The graft polymerization can be carried out at atmospheric pressure, and also at elevated or reduced pressure. Polymerization initiators for the graft polymerization are known and are given, for example, in DE-A-3709921. The K value according to Fikentscher (Cellulose Chemie, vol. 13, 48-64 and 71-74 (1932)) at 25° C. in a 1% strength by weight solution in tetrahydrofuran, of the graft copolymers to be used as protective colloids is 25 to 100, preferably 34 to 65. The optimum amount of protected colloid is influenced firstly by the protective colloid itself, and secondly by the reaction temperature, the desired microcapsule size and the formaldehyde resin mixture. Simple series of experiments can readily determine the optimum amount required. To prepare the water-in-oil emulsion, the protective colloid is generally used in an amount of from 5 to 30% by weight, based on the hydrophobic phase.

The process for the preparation of the microcapsules according to the invention is generally carried out by emulsifying a mixture comprising the hydrophilic component, optionally a hydrophilic medium, and the component B and at least one hydrophobic protective colloid with the in the hydrophobic solvent and component A to give fine droplets, it being possible to adjust the droplet size depending on the intended application purpose. Dispersion of the core material is carried out in a known manner depending on the size of the capsules to be prepared. For the preparation of large capsules, dispersion using effective stirrers, in particular propeller or impeller stirrers, suffices. Small capsules, particularly if the size is to be below 50 μm, require homogenizers or dispersion machines, with or without forced-flow means. The homogenization can also be carried out using ultrasound (e.g. Branson Sonifier II 450). For homogenization by means of ultrasound, suitable equipment is, for example, that described in GB 2250930 and U.S. Pat. No. 5,108,654. The capsule size can be controlled via the speed of the dispersion apparatus/homogenization apparatus and/or using the concentration of the protective colloids or via the molecular weight thereof, i.e. via the viscosity of the aqueous continuous phase, within certain limits. Here, as the speed increases up to a limiting speed, the size of the dispersed particles decreases. In this connection, it is advantageous that the dispersion apparatuses are used at the start of the capsule formation. In the case of continuously operating apparatus with forced-flow, it is advantageous to pass the emulsion through the shear field a number of times. The conditions optimum for individual cases, such as temperature, pH and stirrer speed, can be readily determined by a few experiments.

A "stable dispersion" in the sense of the present invention denotes a dispersion of microcapsules which, upon visible inspection, shows no sign of phase separation, such as creaming, settling, precipitation or coagulation when stored for a period of two weeks at a temperature of 50° C.

The term "aqueous solution" in the sense of the invention denotes water and mixtures of water with at least one at least partly water-miscible organic solvent. Suitable organic solvents are e.g. $C_1$-$C_4$-alkanols. The $C_1$-$C_4$-alkanols are preferably selected from among methanol, ethanol, n-propanol, isopropanol and n-butanol. Mixtures of at least one $C_1$-$C_4$-alkanol with water preferably comprise from 0.1 to 99.9% by weight, particularly preferably from 0.2 to 50% by weight, in particular from 0.3 to 10% by weight of at least one $C_1$-$C_4$-alkanol, based on the total weight of the mixture. In a special embodiment the aqueous solution consists of water.

A further aspect of the invention relates to the processes according to the invention, wherein the obtained microcapsule dispersion described in embodiment (1) as described above, may be dryed to provide microcapsules in solid form, preferably in form of a powder. In another embodiment, the process according to the invention comprising an additional drying step subjecting the microcapsules or microcapsule dispersion obtained by the process described above in embodiments (1) to a drying. The microcapsules or the microcapsule dispersion may be dried using techniques known in the art. For example, the solid capsules can be isolated by filtration and dryed. Drying of the isolated capsules may be performed by heating, e.g. in an oven or by contact with a heated gas stream. Preferably, drying of the dispersion is carried out by spray drying or fluid-bed drying. Spray drying techniques and apparatus are well known in the art. A spray-drying process pushes suspended capsules through a nozzle and into a drying chamber. The capsules may be entrained in a fluid (such as air) that moves inside of a drying chamber. The fluid (which may be heated, for example at a temperature of 150 and 120° C., more preferably between 170° C. and 200° C., and still more preferably between 175° C. and 185° C.) causes the liquid to evaporate, leaving behind the dried capsules which can then be collected from the process equipment and further processed. It is conventional to mix spray dried capsules with flow aids to produce a flowable powder that are not susceptible to caking. Flow aids include silicas or silicates, such as precipitated, fumed or colloidal silicas; starches; calcium carbonate; sodium sulphate; modified cellulose; zeolites; or other inorganic particulates known in the art. It is quite common, given the high temperatures and impaction forces encountered during a spray drying procedure, for core shell capsules to lose some of their core material. Furthermore, it may not be possible to work at sufficiently high temperatures for a sufficiently long period of time to drive off all moisture from the dispersion, without compromising the thermal stability of the capsules. Accordingly, the capsules emerging from a spray-drying process, as herein described, may contain small amounts of surface oil as well as residual moisture.

If the microcapsules or microcapsule dispersion of the present invention, irrespectively of its core material, are intended to be stored in the form of a dispersion, the pH of the dispersion is adjusted to a level of about 5 to 10. This may be achieved with the addition to an alkaline dispersion of a suitable acid, such as citric acid or formic acid.

In a further embodiment, the microcapsule or microcapsules or dispersion of the microcapsules, irrespectively of its core material, may contain non-encapsulated, i.e. free hydrophilic components, external of the capsules in the aqueous dispersion.

It is likewise possible for the ingredients of the core to migrate from the core of the microcapsules (i.e. the hydrophillic component and/or further materials present in the core) into the shell.

In a further embodiment of the invention, the microcapsule or microcapsules or dispersion of the microcapsules irrespectively of its core material, comprises at least one preservative in order to prevent microbial contamination of the microcapsules. The preservative may be contained in the aqueous suspending medium of the dispersion. Suitable preservatives include quaternary compounds, biguanide compounds, ethylhexylglycerin, caprylyl glycol, phenezhyl alcohol, propandiol, undecyl alcohol, tocopherol and mixtures thereof. Non-limiting examples of quaternary compounds include benzalkonium chlorides and/or substituted benzalkonium chlorides, di($C_6$-$C_{14}$)alkyl di short chain ($C_{1-4}$ alkyl and/or hydroxyalkl) quaternary, N-(3-chloroallyl) hexaminium chlorides, benzethonium chloride, methylbenzethonium chloride, cetylpyridinium chloride, diester quaternary ammonium compounds and mixtures thereof. Preferred commercially available benzalkonium chlorides are sold by Lonza under the trademark Barquat®, Maquat® trademarks from Mason, Variquat® trademarks from Witco/Sherex and Hyamine® trademarks from Lonza. Preferred commercially available di($C_6$-$C_{14}$)alkyl di short chain ($C_{1-4}$ alkyl and/or hydroxyalkl) quaternary are sold by Lonza under the trademark Bardac®. Preferred commercially available N-(3-chloroallyl) hexaminium chlorides are sold by Dow under the trademark Dowicide® and Dowicil®. Preferred commercially available benzethonium chlorides are sold by Rohm & Haas under the trademark Hyamine®. Preferred commercially available methylbenzethonium chlorides are sold by Rohm & Haas under the trademark Hyamine® 10*. Preferred commercially available cetylpyridinium chlorides are sold by Merrell Labs under the trademark Cepacol chloride. Examples of preferred dialkyl quaternary compounds are di($C_8$-$C_{12}$)dialkyl dimethyl ammonium chlorides. Preferred commercially available dialkyl quaternary and dioctyldimethylammonium chlorides are sold by Lonza under the trademark Bardac® 22 and (Bardac® 2050). The quaternary compounds useful as cationic preservatives and/or antimicrobial agents herein are preferably selected from the group consisting of dialkyldimethylammonium chlorides, alkyldimethylbenzylammonium chlorides, dialkylmethylbenzylammonium chlorides, and mixtures thereof. Other preferred cationic antimicrobial actives useful herein include diisobutylphenoxyethoxyethyl dimethylbenzylammonium chloride and (methyl)diisobutylphenoxyethoxyethyl dimethylbenzylammonium chloride (i.e. methylbenzethonium chloride). Preferred commercially available quaternary compounds are sold by Rohm & Haas under the trademark Hyamine® 1622. Preferred commercially available preservatives are sold by Schülke under the trademark Sensiva PA20, Sensiva PA40, Sensiva SC10, Sensiva SC50.

The microcapsule composition, microcapsules and dispersion of microcapsules as defined above can be used in a large number of different applications, depending on the type of lipophilic component. A preferred embodiment of the invention is the use of the microcapsule or of microcapsules dispersion irrespectively of its core, material according to the invention for a personal care composition or a composition used for industrial or institutional or hospital disinfection, a material protection composition or a pharmaceutical composition or a plant protection composition or home care products. A preferred embodiment of the invention is the use of the microcapsules or of microcapsules dispersion irrespectively of its core material according to the invention for a cosmetic composition, a hygiene composition, a composition for industrial or institutional or hospital cleaning or disinfection, laundry detergents, fabric softeners, dishwashing liquids, household cleaners or industrial cleaners, oil recovery, adhesives, coatings, or constructions, or agro formulations.

Preference is given to using the microcapsules for the finishing of all kind of nonwovens, like wipes (for example wet wipes or dry wipes for cosmetic or cleaning purposes), but also for finishing papers (including wallpapers, toilet paper or papers for books and newsletters), for finishing diapers or sanitary napkins and similar hygienic products or textiles, e.g. in order to finish the papers or textiles with a dye or an insecticide, or in cosmetic compositions, e.g. for producing sunscreen compositions which comprise the UV filter in the form of the microcapsules. Another use pertains to finishing diapers or sanitary napkins and similar hygienic products. Furthermore the microcapsules may be used in massage oils or cremes or personal lubricants, and suppositories, e.g. to provide this products with antiinflammatory actives. A preferred embodiment of the invention is the use of the microcapsules or of microcapsules dispersion according to the invention in finishing of textiles, papers or nonwovens.

A further aspect of the present invention is the use of a microcapsule dispersion as described above or obtained by the above-described process in a pharmaceutical composition. Suitable pharmaceutical active substances and prodrugs include benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, antiparkinsonians and other antihyperkinetic agents, ophthalmics, neuropathy preparations, calcium metabolism regulators, muscle relaxants, narcotics, antilipemics, hepatic therapeutic agents, coronary agents, cardiacs, immunotherapeutics, regulatory peptides and their inhibitors, hypnotics, sedatives, gynecological agents, antigouts, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta-receptor blockers, calcium antagonists, ACE inhibitors, antiarteriosclerotics, antiinflammatories, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents. Examples of suitable pharmaceutical active substances are in particular the active substances mentioned in paragraphs 0105 to 0131 of US 2003/0157170. The formulation base of pharmaceutical compositions preferably comprises at least one pharmaceutically acceptable auxiliary. Pharmaceutically acceptable auxiliaries are auxiliaries which are known for use in the field of pharmaceuticals, food technology and related fields, in particular those listed in the relevant pharmacopoeias (e.g., DAB, Ph. Eur., BP, NF), and other auxiliaries, the properties of which do not preclude a physiological application.

A further aspect of the present invention is the use of a microcapsule dispersion as described above or obtained by the above-described process in a cosmetic composition. Suitable cosmetically active substances and cosmetic auxiliaries are described in Karl-Heinz Schrader, Grundlagen und Rezepturen der Kosmetika [Fundamentals and formulations of cosmetics], 2nd edition, Verlag Hüthig, Heidelberg, which is hereby incorporated by reference. Suitable cosmetic auxiliaries are described, for example, in Fiedler, H. P., Lexikon der Hilfsstoffe für Pharmazie, Kosmetik und angrenzende Gebiete [Encyclopedia of Auxiliaries for Pharmaceuticals, Cosmetics and Related Fields], 4th edition, Aulendorf: ECV-Editio-Kantor-Verlag, 1996. Suitable cosmetic auxiliaries can be lubricants, wetting agents, emulsifying and suspending agents, preservatives, antioxidants, antiirritatives, chelating agents, emulsion stabilizers, filmforming agents, gel formers, odor-masking agents, resins, hydrocolloids, solvents, solubility promoters, neutralizing agents, permeation accelerators, pigments, quaternary ammonium compounds, refatting and superfatting agents, ointment, cream or oil base substances, silicone derivatives, stabilizers, sterilants, propellants, drying agents, opacifiers, thickeners, waxes, softeners or white oils.

A further aspect of the present invention is the use of a microcapsule dispersion as described above or obtained by the above-described process in a hygiene composition. A further aspect of the present invention is the use of a microcapsule dispersion as described above or obtained by the above-described process in a composition for industrial or institutional or hospital cleaning disinfection. A further aspect of the present invention is the use of a microcapsule dispersion as described above or obtained by the above-described process in a laundry detergents. A further aspect of the present invention is the use of a microcapsule dispersion as described above or obtained by the above-described process in a fabric softeners. A further aspect of the present invention is the use of a microcapsule dispersion as described above or obtained by the above-described process in a dishwashing liquids. A further aspect of the present invention is the use of a microcapsule dispersion as described above or obtained by the above-described process in a household cleaners. A further aspect of the present invention is the use of a microcapsule dispersion as described above or obtained by the above-described process in a industrial cleaners. A further aspect of the present invention is the use of a microcapsule dispersion as described above or obtained by the above-described process in oil recovery. A further aspect of the present invention is the use of a microcapsule dispersion as described above or obtained by the above-described process in a adhesive. A further aspect of the present invention is the use of a microcapsule dispersion as described above or obtained by the above-described process in coatings. A further aspect of the present invention is the use of a microcapsule dispersion as described above or obtained by the above-described process in or as construction additives composition. Suitable construction additives are selected from plasticizers, superplasticizers, shrinkage reducing agents, corrosion inhibitors, defoaming agents, retardants, accelerators, seeding agents, concrete levelling agents, hydrophobization agents, accelerators for cementitious systems and mixtures thereof. Suitable hydrophobization and shrinkage reducing agents are silicon oil, reactive siloxanes, calcium soaps e.g. calcium stearate; hemiterpene alcohol e.g. isoprenol and fluore-based organo-compounds.

A further aspect of the present invention is the use of a microcapsule dispersion as described above or obtained by the above-described process in agro formulations. When used in agro formulations the hydrophilic component usually comprises a pesticide.

The microcapsules comprising a hydrophilic component selected from pesticides may optionally comprise auxiliaries which are customary in agrochemical formulations. The auxiliaries used depend on the particular application form and active substance, respectively. Examples for suitable auxiliaries are dispersants or emulsifiers (such as further solubilizers, protective colloids, surfactants and adhesion agents), organic and anorganic thickeners, bactericides, antifreezing agents, anti-foaming agents, if appropriate colorants and tackifiers or binders (e. g. for seed treatment formulations). Examples for suitable auxiliaries are solvents, liquid carriers, solid carriers or fillers, surfactants, further dispersants, emulsifiers, wetters, further adjuvants, solubilizers, penetration enhancers, protective colloids, adhesion agents, thickeners, humectants, repellents, attractants, feeding stimulants, compatibilizers, bactericides, antifreezing agents, anti-foaming agents, colorants, tackifiers and binders. Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

The present invention furthermore relates to a method of controlling phytopathogenic fungi and/or undesired plant growth and/or undesired insect or mite attack and/or for regulating the growth of plants, wherein the microcapsules or the microcapsule dispersion, where the hydrophobic component comprises a pesticide, are allowed to act on the respective pests, their environment or the crop plants to be protected from the respective pest, on the soil and/or on undesired plants and/or on the crop plants and/or on their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (*Stevia rebaudania*); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The user applies the microcapsule or the microcapsule dispersion usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, very preferably 50 to 200 liters of the ready-to-use spray liquor are applied per hectare of agricultural useful area.

EXAMPLES

The following examples are intended to further illustrate the present invention without limiting its scope in any way.

Determination of the Isocyanate Content was made as follows: Samples were taken from the reaction mixture. Approximately 0.5 g were weighted on an analytical balance. 100 mL NMP and 25 mL dibutylamine were added. The mixture was titrated with 0.1 M hydrochloric acid using a solvent pH-electrode and a Metrohm titration system.

Determination of the Water Content and the Hydroxyl Groups was performed with Karl-Fischer method according to DIN 51777 and DIN 53240.

Isopar® G: Isoparaffinic fluid, distillation range 161-173° C.
Protective Colloid A: Copolymer of methyl methacrylate, stearyl methacrylate, acrylic acid and methacrylic acid.
Poly-L-lysine was used as solution in water with $M_w$~2000 Da (20% α-polylysine and 80% ε-polylysine), amine number 200 mg KOH/g.
Polyester-Polyol A was a reaction product of trimethylolpropan (TMP) and ε-caprolacton, a clear liquid with hydroxy value of 564 mg KOH/g, acid value below 1 mg KOH/g, mean molecular weight 300 g/mol, and a viscosity of about 170 mPas (60° C.).
Green Dye: D&C Green No. 5, CAS 4403-90-1, water soluble green dye.

Synthesis of NCO-Functionalized Oligoester (Product A)

A mixture of 107 g Polyester-Polyol A, 100 g 2-heptanone and 47.9 g Isophoronediisocyanate (IPDI) was heated to 100° C. and gently stirred. The NCO-content was regularly measured to ensure the conversion rate. NCO content before reaction was about 15.96%. NCO content at the end of the reaction was about 7.29%. This indicated that all hydroxy groups of the Polyester-Polyol A were modified with an IPDI molecule.

Example 1: Microcapsules with Polylysine

|  |  | Quantity [g] | Concentration [%] |
|---|---|---|---|
| Charge | Isosopar ® G | 59.60 | 100 |
|  | Protective Colloid A | 8.82 | 25 |
| Feed 1 | Water | 18.45 | 100 |
|  | Sodium Chloride | 0.99 | 100 |
|  | Polylysine | 0.72 | 55 |
|  | Green Dye | 0.4 | 100 |
| Feed 2 | Product A | 1.48 | 60 |
|  | 2-Heptanone | 9.54 | 100 |

Feed 1 was dissolved separately, and then the Charge and the Feed 1 were added in a reactor and emulsified for 10 min at 25000 rpm. Feed 2 was added to the stirred reactor within 60 min. Next the reactor was heated in 60 min to 80° C., kept for 2 h at this temperature and finally cooled down to room temperature.

Example 2: Microcapsules with TEPA

|  |  | Quantity [g] | Concentration [%] |
|---|---|---|---|
| Charge | Isosopar ® G | 59.60 | 100 |
|  | Protective Colloid A | 8.82 | 25 |
| Feed 1 | Water | 18.79 | 100 |
|  | Sodium Chloride | 0.99 | 100 |
|  | Tetraethylene pentamine | 0.16 | 100 |
|  | Green Dye | 0.06 | 100 |
| Feed 2 | Product A | 2.04 | 60 |
|  | 2-Heptanone | 9.54 | 100 |

The microcapsules were prepared as described in Example 1.

Example 3: Microcapsules with Polylysine

|  |  | [%] by weight | Concentration [%] |
|---|---|---|---|
| Charge | Isosopar ® G | 61.09 | 100 |
|  | Protective Colloid A | 8.82 | 25 |
| Feed 1 | Water | 18.66 | 100 |
|  | Sodium Chloride | 0.88 | 100 |
|  | Polylysine | 1.44 | 55 |
|  | Green Dye | 0.09 | 100 |
| Feed 2 | Product A | 2.97 | 60 |
|  | 2-Heptanone | 8.06 | 100 |

The microcapsules were prepared as described in Example 1.

Example 4: Microcapsules with IPDI Instead of Product A (Comparative)

|  |  | [%] by weight | Concentration [%] |
|---|---|---|---|
| Charge | Isosopar ® G | 59.69 | 100 |
|  | Protective Colloid A | 8.82 | 25 |
| Feed 1 | Water | 18.79 | 100 |
|  | Sodium Chloride | 0.99 | 100 |
|  | Tetraethylene pentamine | 0.64 | 100 |
|  | Green Dye | 0.06 | 100 |
| Feed 2 | IPDI | 1.56 | 100 |
|  | 2-Heptanone | 9.46 | 100 |

The microcapsules were prepared as described in Example 1.

Example 5: Microcapsules with IPDI Instead of Product A (Comparative)

|  |  | [%] by weight | Concentration [%] |
|---|---|---|---|
| Charge | Isosopar ® G | 58.73 | 100 |
|  | Protective Colloid A | 8.82 | 25 |
| Feed 1 | Water | 18.79 | 100 |
|  | Sodium Chloride | 0.99 | 100 |
|  | Polylysine | 1.58 | 55 |
|  | Green Dye | 0.06 | 100 |
| Feed 2 | IPDI | 0.63 | 100 |
|  | 2-Heptanone | 10.41 | 100 |

The microcapsules were prepared as described in Example 1.

Example 6: Analytic Results of the Capsule Suspensions

The capsule size was determined by Dynamic Light Scattering. Measurements were performed using a Malvern Particle Sizer 3600E type, and following a standard procedure described in the literature. D (0.5) is the median diameter of the volume of distribution. It is expressed in microns, and it indicates that 50% of the sample has a size smaller than that value, whereas 50% have a larger size.

|  | D (0.5) |
| --- | --- |
| Example 1 | 0.315 μm |
| Example 2 | 0.511 μm |
| Example 3 | 0.347 μm |
| Example 4[a)] | 0.685 μm |
| Example 5[a)] | 0.650 μm |

[a)] comparative

The results demonstrated that the inventive microcapsules had smaller particle size as microcapsules based on the hardly biodegradable isocyanate isophorone diisocyanate used in Example 4 and 5. For comparison, the poly(ester-urethane) containing at least 2 isocyanate groups (component A) of the present invention has several ester bonds which allow for a good biodegradability of this microcapsule type, e.g. at smaller similar particle size.

Example 7: Pesticidal Microcapsules with Polylysine

|  |  | Quantity [g] | Concentration [%] |
| --- | --- | --- | --- |
| Charge | Isosopar ® G | 59.60 | 100 |
|  | Protective Colloid A | 8.82 | 25 |
| Feed 1 | Water | 18.45 | 100 |
|  | Sodium Chloride | 0.99 | 100 |
|  | Polylysine | 0.72 | 55 |
|  | Pesticide | 0.4 | 100 |
| Feed 2 | Product A | 1.48 | 60 |
|  | 2-Heptanone | 9.54 | 100 |

The microcapsules are prepared as described in Example 1. Instead of the water-soluble dye water-soluble pesticides are used:

Example 7A): glyphosate potassium salt (water solubility >500 g/l at 20° C.)

Example 7B): dicamba sodium salt (water solubility >100 g/l at 20° C.)

The particle size are determined as in Example 6 and the results are similar to those of Example 1 in the Table of Example 6.

Example 8: Pesticidal Microcapsules with TEPA

|  |  | Quantity [g] | Concentration [%] |
| --- | --- | --- | --- |
| Charge | Isosopar ® G | 59.60 | 100 |
|  | Protective Colloid A | 8.82 | 25 |
| Feed 1 | Water | 18.79 | 100 |
|  | Sodium Chloride | 0.99 | 100 |
|  | Tetraethylene pentamine | 0.16 | 100 |
|  | Pesticide | 0.06 | 100 |
| Feed 2 | Product A | 2.04 | 60 |
|  | 2-Heptanone | 9.54 | 100 |

The microcapsules are prepared by the operation mode as described in Example 2. Instead of the water-soluble dye water-soluble pesticides are used:

Example 8A): glyphosate potassium salt (water solubility >500 g/l at 20° C.)

Example 8B): dicamba sodium salt (water solubility >100 g/l at 20° C.)

The particle size is determined as in Example 5 and the results are similar to those of Example 2 in the Table of Example 5.

The invention claimed is:

1. A microcapsule comprising a capsule core and a polymeric shell, wherein the core comprises only hydrophilic components, and the shell comprises, in polymerized form, the following components:
   A) at least one poly(ester-urethane) containing at least 2 isocyanate groups, obtained through reacting at least one polyester-polyol containing at least 2 OH groups with at least one polyisocyanate containing at least 2 NCO groups, and
   B) at least one compound comprising at least 2 terminal groups that are reactive towards isocyanate-groups, that are selected from OH, NHR, or SH, wherein R is selected from hydrogen, alkyl, cycloalkyl, or aryl.

2. The microcapsule according to claim 1, wherein the poly(ester-urethane) is the reaction product of the polyester-polyol with the polyisocyanate selected from hexamethylene diisocyanate, tetramethylene diisocyanate, dicyclohexylmethane-4,4'-diisocyanate, isophoronediisocyanate, 2,4- and 2,6-toluylene diisocyanate and isomer mixtures thereof, 2,4'- and 4,4'-diphenylmethane diisocyanate and isomer mixtures, biurets, allophanates and/or isocyanurates or mixtures thereof.

3. The microcapsules according to claim 1, wherein the polyester-polyol is a polylactonpolyol that contains 2 or 3 OH groups.

4. The microcapsules according to claim 1, wherein the polyester-polyol is a compound of the formulae (2), (5), or mixtures thereof,

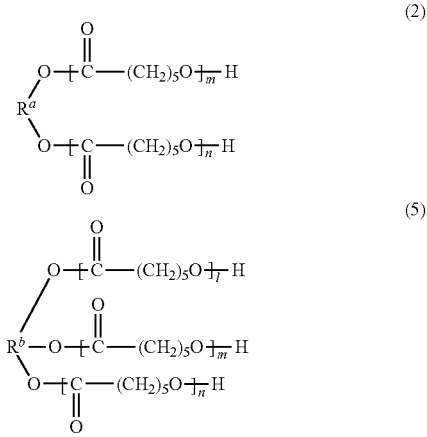

wherein
$R^a$ is selected from linear or branched C1-C10-alkylene group and C3-C20-cycloaliphatic radicals having 3 to 10 ring carbon atoms,
$R^b$ is a linear or branched C1-C10-alkantriyl group,
l, m, and n are independently an integer of 1 to 100,
with the proviso that
for the formula (2), n+m is an integer of 2 to 100, and
for the formula (5), n+m+l is an integer of 2 to 100.

5. The microcapsules according to claim 1, wherein the polyester-polyol has a weight-average molecular weight of from 200 to 3000 g/mol.

6. The microcapsule according to claim 1, wherein the component B) is selected from diols, diamines, aminoalcohols, polymeric polyols having at least 3 OH groups, polymeric polyamines heaving at least 3 primary or secondary amino groups, and mixtures thereof.

7. The microcapsule according to claim 1, wherein the component B) comprises a polyfunctional amine.

8. The microcapsule according to claim 1, wherein the component B) comprises a polyfunctional amine selected from the group consisting of polyamidoamines and polyethyleneimines.

9. The microcapsule according to claim 1, wherein the core-shell ratio (w/w) of the microcapsules is 20:1 to 1:1.

10. The microcapsule according to claim 1, wherein the microcapsules have a mean particle size d (0.5) in the range of 0.1 m to 50 m.

11. The microcapsule according to claim 1, wherein the hydrophilic components have a solubility in water of at least 1 g/l at room temperature.

12. The microcapsule according to claim 1, wherein the hydrophilic component comprises a pesticide.

13. A microcapsule dispersion comprising the microcapsules according to claim 1.

14. A process for the preparation of the microcapsules according to claim 1, wherein the core comprises hydrophilic components, the process comprising the steps:
 a) providing a premix (Ia) comprising the hydrophilic components to be encapsulated (Ca), and the at least one component (B), and
 b) mixing the premix (Ia) provided in step a) with a hydrophobic medium (IIa) comprising at least one hydrophobic protective colloid, the at least one component (A), and reacting the resulting mixture to form the microcapsules of claim 1 dispersed in the hydrophobic medium (IIa).

15. A method of controlling phytopathogenic fungi, controlling undesired plant growth, controlling undesired insect or mite attack, or for regulating the growth of plants, wherein the microcapsules according to claim 1 comprise a pesticide and are allowed to act on the respective pests, the environment of the respective pests, the crop plants to be protected from the respective pest, the soil, undesired plants, the crop plants, or the environment of the crop plants.

16. The microcapsule according to claim 6, wherein the component B) is selected from hexamethylene diamine, ethylenediamine, N-ethylethylenediamine, N,N'-diethylethylenediamine, diethylenetriamine, tetraethylene pentamine, spermine, spermidine, polyaminosaccharides, polyvinylamines polyetheramines, polyesteramines, polyaminoacids and polyamidoamines, and mixtures thereof.

17. The microcapsule according to claim 9, wherein the core-shell ratio (w/w) of the microcapsules is 10:1 to 3:1.

18. The microcapsule according to claim 10, wherein the mean particle size d (0.5) is in the range from 0.1 μm to 0.8 μm.

19. The microcapsule according to claim 11, wherein the hydrophilic components have a solubility in water of at least 20 g/l at room temperature.

20. The microcapsule according to claim 12, wherein the hydrophilic component further comprises water.

* * * * *